(12) United States Patent
Feng et al.

(10) Patent No.: US 11,167,039 B2
(45) Date of Patent: Nov. 9, 2021

(54) MET ANTIBODY DRUG CONJUGATES

(71) Applicant: Eli Lilly and Company, Indianapolis, IN (US)

(72) Inventors: Yiqing Feng, Carmel, IN (US); Philip Arthur Hipskind, New Palestine, IN (US); Renhua Li, Fishers, IN (US); Ling Liu, Carmel, IN (US); Takako Wilson, Indianapolis, IN (US); Aaron David Wrobleski, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 81 days.

(21) Appl. No.: 16/346,260

(22) PCT Filed: Nov. 17, 2017

(86) PCT No.: PCT/US2017/062247
§ 371 (c)(1),
(2) Date: Apr. 30, 2019

(87) PCT Pub. No.: WO2018/098035
PCT Pub. Date: May 31, 2018

(65) Prior Publication Data
US 2020/0061204 A1    Feb. 27, 2020

Related U.S. Application Data

(60) Provisional application No. 62/425,853, filed on Nov. 23, 2016.

(51) Int. Cl.
*A61K 47/68* (2017.01)
*A61P 35/00* (2006.01)

(52) U.S. Cl.
CPC ...... *A61K 47/6851* (2017.08); *A61K 47/6871* (2017.08); *A61P 35/00* (2018.01)

(58) Field of Classification Search
CPC ............ A61K 47/6851; A61K 47/6871; A61K 47/6857; A61P 35/00
See application file for complete search history.

(56) References Cited

U.S. PATENT DOCUMENTS

2017/0348429 A1* 12/2017 Reilly et al. ........... A61K 47/68

FOREIGN PATENT DOCUMENTS

| WO | 2007/011968 A2 | 1/2007 |
| WO | 2010/059654 A1 | 5/2010 |
| WO | 2012/153193 A2 | 11/2012 |
| WO | 2016/094455 A1 | 6/2016 |

OTHER PUBLICATIONS

Van Geel, R., et al., "Chemoenzymatic conjugation of toxic payloads to the globally conserved N-glycan of native mAbs provides homogeneous and highly efficacious antibody—drug conjugates." Bioconjugate Chemistry 26, No. 11 (2015): 2233-2242.
Kiyotaka, Y., et al., "A phase I dose-escalation study of LY2875358, a bivalent MET antibody, given as monotherapy or in combination with erlotinib or gefitinib in Japanese patients with advanced malignancies." Investigational New Drugs 34, No. 5 (2016): 584-595.
International Search Report for PCT/US2017/062247 (dated Mar. 1, 2018).
Written Opinion for PCT/US2017/062247 (dated Mar. 1, 2018).
Strickler, JH, et al., "Phase 1, open-label, dose-escalation and expansion study of ABBV-399, an antibody drug conjugate (ADC) targeting c-Met, in patients (pts) with advanced solid tumors," Journal of Clinical Oncology, vol. 34, No. 15, Supplement, 2510 (May 20, 2016).
Birrer MJ, et al., "Antibody-Drug Conjugate-Based Therapeutics: State of the Science," *JNCI J. Natl. Cancer Inst.* 2019; 111(6): 538-549, doi: 10.1093/jnci/djz035 (2019).
Jain N, et al., "Current ADC Linker Chemistry," *Pharm Res.* 2015; 32: 3526-3540 (2015).
Liu L, et al., "Abstract 353: A novel molecule with profound tumor killing activity," *Cancer Research* 2019; 79(13) Supplement, DOI: 10.1158/1538-7445.AM2019-353 (2019).
Sau S, et al., "Advances in antibody-drug conjugates: A new era of targeted cancer therapy," *Drug Discovery Today* 2017; 10: 1547-1556 (2017).
Reply to Office Action in U.S. Appl. No. 15/910,788, filed Sep. 20, 2018.
Reply to Office Action in U.S. Appl. No. 15/910,788, filed Mar. 1, 2019.

* cited by examiner

*Primary Examiner* — Hong Sang
*Assistant Examiner* — Sung Min Yoon
(74) *Attorney, Agent, or Firm* — Quarles & Brady LLP

(57) ABSTRACT

Provided are antibody-drug conjugates (ADCs) that bind to, and kill MET expressing tumor cells, and that are effective in treating MET expressing cancers. Also provided are novel compounds and methods of conjugating MET antibodies to generate such ADCs.

13 Claims, 11 Drawing Sheets

Specification includes a Sequence Listing.

SEQUENCE LISTING

<160> NUMBER OF SEQ ID NOS: 24

<210> SEQ ID NO 1
<211> LENGTH: 10
<212> TYPE: PRT
<213> ORGANISM: Artificial Sequence
<220> FEATURE:
<223> OTHER INFORMATION: Synthetic construct

<400> SEQUENCE: 1

Gly Tyr Thr Phe Thr Asp Tyr Tyr Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Arg Val Asn Pro Asn Arg Arg Gly Thr Thr Tyr Asn Gln Lys Phe Glu
1               5                   10                  15

Gly

<210> SEQ ID NO 3
<211> LENGTH: 8
<212> TYPE: PRT
<213> ORGANISM: ARTIFICIAL SEQUENCE
<220> FEATURE:
<223> OTHER INFORMATION: Synthetic Construct

<400> SEQUENCE: 3

Ala Arg Ala Asn Trp Leu Asp Tyr
1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic Construct

<400> SEQUENCE: 4

Ser Val Ser Ser Ser Val Ser Ser Ile Tyr Leu His
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Tyr Ser Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Val Tyr Ser Gly Tyr Pro Leu Thr
1               5

<210> SEQ ID NO 7
<211> LENGTH: 115
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
            35                  40                  45

Gly Arg Val Asn Pro Asn Arg Arg Gly Thr Thr Tyr Asn Gln Lys Phe
        50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
            100                 105                 110

Val Ser Ser
        115

<210> SEQ ID NO 8
<211> LENGTH: 108
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Val Ser Ser Ile
                20                  25                  30

Tyr Leu His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Ser Gly Tyr Pro
                85                  90                  95

Leu Thr Phe Gly Gly Gly Thr Lys Val Glu Ile Lys
            100                 105

<210> SEQ ID NO 9
<211> LENGTH: 215
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 9

Asp Ile Gln Met Thr Gln Ser Pro Ser Ser Leu Ser Ala Ser Val Gly

```
                1               5              10              15
            Asp Arg Val Thr Ile Thr Cys Ser Val Ser Ser Val Ser Ser Ile
                                20                  25                  30

Tyr Leu His Trp Tyr Gln Gln Lys Pro Gly Lys Ala Pro Lys Leu Leu
                            35                  40                  45

Ile Tyr Ser Thr Ser Asn Leu Ala Ser Gly Val Pro Ser Arg Phe Ser
                        50                  55                  60

Gly Ser Gly Ser Gly Thr Asp Phe Thr Leu Thr Ile Ser Ser Leu Gln
             65                  70                  75                  80

Pro Glu Asp Phe Ala Thr Tyr Tyr Cys Gln Val Tyr Ser Gly Tyr Pro
                            85                  90                  95

Leu Thr Phe Gly Gly Gly Thr Lys Val Glu Ile Lys Arg Thr Val Ala
                        100                 105                 110

Ala Pro Ser Val Phe Ile Phe Pro Pro Ser Asp Glu Gln Leu Lys Ser
                        115                 120                 125

Gly Thr Ala Ser Val Val Cys Leu Leu Asn Asn Phe Tyr Pro Arg Glu
                        130                 135                 140

Ala Lys Val Gln Trp Lys Val Asp Asn Ala Leu Gln Ser Gly Asn Ser
            145                 150                 155                 160

Gln Glu Ser Val Thr Glu Gln Asp Ser Lys Asp Ser Thr Tyr Ser Leu
                            165                 170                 175

Ser Ser Thr Leu Thr Leu Ser Lys Ala Asp Tyr Glu Lys His Lys Val
                        180                 185                 190

Tyr Ala Cys Glu Val Thr His Gln Gly Leu Ser Ser Pro Val Thr Lys
                        195                 200                 205

Ser Phe Asn Arg Gly Glu Cys
                        210                 215

<210> SEQ ID NO 10
<211> LENGTH: 651
<212> TYPE: DNA
<213> ORGANISM: Artificial sequence
<220> FEATURE:
<223> OTHER INFORMATION: Synthetic Construct

<400> SEQUENCE: 10
gacatccaga tgacccagtc tccatcctcc ctgtctgcat ctgtaggaga cagagtcacc    60
atcacttgca gtgtcagctc aagtgtatcc tccatttact gcactggta tcagcagaaa   120
ccagggaaag cccctaagct cctgatctat agcacatcca acttggcttc tggagtccca   180
tcaaggttca gtggcagtgg atctgggaca gatttcactc tcaccatcag cagtctgcaa   240
cctgaagatt ttgcaactta ctactgtcaa gtctacagtg gttacccgct cacgttcggc   300
ggagggacca aggtggagat caaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgctaata g             651

<210> SEQ ID NO 11
<211> LENGTH: 932
<212> TYPE: PRT
<213> ORGANISM: ARTIFICIAL SEQUENCE
<220> FEATURE:
```

<223> OTHER INFORMATION: SYNTHETIC CONSTRUCT

<400> SEQUENCE: 11

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400
```

```
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
            420                 425                 430
Gln Phe Ser Glu Val Leu Leu Thr Ser Ile Ser Thr Phe Ile Lys Gly
        435                 440                 445
Asp Leu Thr Ile Ala Asn Leu Gly Thr Ser Glu Gly Arg Phe Met Gln
450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
            500                 505                 510
Ile Pro Leu Asn Gly Leu Gly Cys Arg His Phe Gln Ser Cys Ser Gln
        515                 520                 525
Cys Leu Ser Ala Pro Pro Phe Val Gln Cys Gly Trp Cys His Asp Lys
    530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
            580                 585                 590
Asn Asn Lys Phe Asp Leu Lys Lys Thr Arg Val Leu Leu Gly Asn Glu
        595                 600                 605
Ser Cys Thr Leu Thr Leu Ser Glu Ser Thr Met Asn Thr Leu Lys Cys
    610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
            660                 665                 670
Thr Leu Leu Thr Leu Thr Gly Asn Tyr Leu Asn Ser Gly Asn Ser Arg
        675                 680                 685
His Ile Ser Ile Gly Gly Lys Thr Cys Thr Leu Lys Ser Val Ser Asn
    690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
            740                 745                 750
Phe Ile Ser Gly Gly Ser Thr Ile Thr Gly Val Gly Lys Asn Leu Asn
        755                 760                 765
Ser Val Ser Val Pro Arg Met Val Ile Asn Val His Glu Ala Gly Arg
    770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
Thr Lys Ala Phe Phe Met Leu Asp Gly Ile Leu Ser Lys Tyr Phe Asp
```

```
                820                 825                 830
Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
        850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
            885                 890                 895

Pro Asn Asp Leu Leu Lys Leu Asn Ser Glu Leu Asn Ile Glu Trp Lys
        900                 905                 910

Gln Ala Ile Ser Ser Thr Val Leu Gly Lys Val Ile Val Gln Pro Asp
            915                 920                 925

Gln Asn Phe Thr
    930

<210> SEQ ID NO 12
<211> LENGTH: 908
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 12

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
    50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
            85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Val Gly Asn Thr
            165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
```

-continued

```
                245                 250                 255
Phe Cys Ser Ile Asn Ser Gly Leu His Ser Tyr Met Glu Met Pro Leu
            260                 265                 270
Glu Cys Ile Leu Thr Glu Lys Arg Lys Lys Arg Ser Thr Lys Lys Glu
        275                 280                 285
Val Phe Asn Ile Leu Gln Ala Ala Tyr Val Ser Lys Pro Gly Ala Gln
    290                 295                 300
Leu Ala Arg Gln Ile Gly Ala Ser Leu Asn Asp Asp Ile Leu Phe Gly
305                 310                 315                 320
Val Phe Ala Gln Ser Lys Pro Asp Ser Ala Glu Pro Met Asp Arg Ser
                325                 330                 335
Ala Met Cys Ala Phe Pro Ile Lys Tyr Val Asn Asp Phe Phe Asn Lys
            340                 345                 350
Ile Val Asn Lys Asn Asn Val Arg Cys Leu Gln His Phe Tyr Gly Pro
        355                 360                 365
Asn His Glu His Cys Phe Asn Arg Thr Leu Leu Arg Asn Ser Ser Gly
    370                 375                 380
Cys Glu Ala Arg Arg Asp Glu Tyr Arg Thr Glu Phe Thr Thr Ala Leu
385                 390                 395                 400
Gln Arg Val Asp Leu Phe Met Gly Gln Phe Ser Glu Val Leu Leu Thr
                405                 410                 415
Ser Ile Ser Thr Phe Ile Lys Gly Asp Leu Thr Ile Ala Asn Leu Gly
            420                 425                 430
Thr Ser Glu Gly Arg Phe Met Gln Val Val Val Ser Arg Ser Gly Pro
        435                 440                 445
Ser Thr Pro His Val Asn Phe Leu Leu Asp Ser His Pro Val Ser Pro
    450                 455                 460
Glu Val Ile Val Glu His Thr Leu Asn Gln Asn Gly Tyr Thr Leu Val
465                 470                 475                 480
Ile Thr Gly Lys Lys Ile Thr Lys Ile Pro Leu Asn Gly Leu Gly Cys
                485                 490                 495
Arg His Phe Gln Ser Cys Ser Gln Cys Leu Ser Ala Pro Pro Phe Val
            500                 505                 510
Gln Cys Gly Trp Cys His Asp Lys Cys Val Arg Ser Glu Glu Cys Leu
        515                 520                 525
Ser Gly Thr Trp Thr Gln Gln Ile Cys Leu Pro Ala Ile Tyr Lys Val
    530                 535                 540
Phe Pro Asn Ser Ala Pro Leu Glu Gly Gly Thr Arg Leu Thr Ile Cys
545                 550                 555                 560
Gly Trp Asp Phe Gly Phe Arg Arg Asn Asn Lys Phe Asp Leu Lys Lys
                565                 570                 575
Thr Arg Val Leu Leu Gly Asn Glu Ser Cys Thr Leu Thr Leu Ser Glu
            580                 585                 590
Ser Thr Met Asn Thr Leu Lys Cys Thr Val Gly Pro Ala Met Asn Lys
        595                 600                 605
His Phe Asn Met Ser Ile Ile Ile Ser Asn Gly His Gly Thr Thr Gln
    610                 615                 620
Tyr Ser Thr Phe Ser Tyr Val Asp Pro Val Ile Thr Ser Ile Ser Pro
625                 630                 635                 640
Lys Tyr Gly Pro Met Ala Gly Gly Thr Leu Leu Thr Leu Thr Gly Asn
                645                 650                 655
Tyr Leu Asn Ser Gly Asn Ser Arg His Ile Ser Ile Gly Gly Lys Thr
            660                 665                 670
```

Cys Thr Leu Lys Ser Val Ser Asn Ser Ile Leu Glu Cys Tyr Thr Pro
                675                 680                 685

Ala Gln Thr Ile Ser Thr Glu Phe Ala Val Lys Leu Lys Ile Asp Leu
            690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Gly Gly Ser Thr Ile
                725                 730                 735

Thr Gly Val Gly Lys Asn Leu Asn Ser Val Ser Val Pro Arg Met Val
            740                 745                 750

Ile Asn Val His Glu Ala Gly Arg Asn Phe Thr Val Ala Cys Gln His
                755                 760                 765

Arg Ser Asn Ser Glu Ile Ile Cys Cys Thr Thr Pro Ser Leu Gln Gln
770                 775                 780

Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
                805                 810                 815

Phe Lys Pro Phe Glu Lys Pro Val Met Ile Ser Met Gly Asn Glu Asn
            820                 825                 830

Val Leu Glu Ile Lys Gly Asn Asp Ile Asp Pro Glu Ala Val Lys Gly
835                 840                 845

Glu Val Leu Lys Val Gly Asn Lys Ser Cys Glu Asn Ile His Leu His
                850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Ile Ser Ser Thr Val Leu
                885                 890                 895

Gly Lys Val Ile Val Gln Pro Asp Gln Asn Phe Thr
            900                 905

<210> SEQ ID NO 13
<211> LENGTH: 283
<212> TYPE: PRT
<213> ORGANISM: Homo sapiens

<400> SEQUENCE: 13

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
    50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu

|   |   |   | 130 |   |   |   | 135 |   |   |   | 140 |   |   |   |

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
                195                 200                 205

Ser Tyr Ile Asp Val Leu Pro Glu Phe Arg Asp Ser Tyr Pro Ile Lys
            210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
                260                 265                 270

Glu Cys Ile Leu Thr Glu Lys Arg Lys Lys Arg
            275                 280

<210> SEQ ID NO 14
<211> LENGTH: 212
<212> TYPE: PRT
<213> ORGANISM: HOMO SAPIENS

<400> SEQUENCE: 14

Ser Thr Lys Lys Glu Val Phe Asn Ile Leu Gln Ala Ala Tyr Val Ser
1               5                   10                  15

Lys Pro Gly Ala Gln Leu Ala Arg Gln Ile Gly Ala Ser Leu Asn Asp
                20                  25                  30

Asp Ile Leu Phe Gly Val Phe Ala Gln Ser Lys Pro Asp Ser Ala Glu
            35                  40                  45

Pro Met Asp Arg Ser Ala Met Cys Ala Phe Pro Ile Lys Tyr Val Asn
50                  55                  60

Asp Phe Phe Asn Lys Ile Val Asn Lys Asn Asn Val Arg Cys Leu Gln
65                  70                  75                  80

His Phe Tyr Gly Pro Asn His Glu His Cys Phe Asn Arg Thr Leu Leu
                85                  90                  95

Arg Asn Ser Ser Gly Cys Glu Ala Arg Arg Asp Glu Tyr Arg Thr Glu
            100                 105                 110

Phe Thr Thr Ala Leu Gln Arg Val Asp Leu Phe Met Gly Gln Phe Ser
            115                 120                 125

Glu Val Leu Leu Thr Ser Ile Ser Thr Phe Ile Lys Gly Asp Leu Thr
130                 135                 140

Ile Ala Asn Leu Gly Thr Ser Glu Gly Arg Phe Met Gln Val Val Val
145                 150                 155                 160

Ser Arg Ser Gly Pro Ser Thr Pro His Val Asn Phe Leu Leu Asp Ser
                165                 170                 175

His Pro Val Ser Pro Glu Val Ile Val Glu His Thr Leu Asn Gln Asn
            180                 185                 190

Gly Tyr Thr Leu Val Ile Thr Gly Lys Lys Ile Thr Lys Ile Pro Leu
            195                 200                 205

Asn Gly Leu Gly
    210

```
<210> SEQ ID NO 15
<211> LENGTH: 10
<212> TYPE: PRT
<213> ORGANISM: HOMO SAPIENS

<400> SEQUENCE: 15

Val Val Asp Thr Tyr Tyr Asp Asp Gln Leu
1               5                   10

<210> SEQ ID NO 16
<211> LENGTH: 26
<212> TYPE: PRT
<213> ORGANISM: HOMO SAPIENS

<400> SEQUENCE: 16

Ile Ser Cys Gly Ser Val Asn Arg Gly Thr Cys Gln Arg His Val Phe
1               5                   10                  15

Pro His Asn His Thr Ala Asp Ile Gln Ser
            20                  25

<210> SEQ ID NO 17
<211> LENGTH: 17
<212> TYPE: PRT
<213> ORGANISM: HOMO SAPIENS

<400> SEQUENCE: 17

Ala Leu Gly Ala Lys Val Leu Ser Ser Val Lys Asp Arg Phe Ile Asn
1               5                   10                  15

Phe

<210> SEQ ID NO 18
<211> LENGTH: 12
<212> TYPE: PRT
<213> ORGANISM: HOMO SAPIENS

<400> SEQUENCE: 18

Val Arg Arg Leu Lys Glu Thr Lys Asp Gly Phe Met
1               5                   10

<210> SEQ ID NO 19
<211> LENGTH: 6
<212> TYPE: PRT
<213> ORGANISM: HOMO SAPIENS

<400> SEQUENCE: 19

Asp Thr Tyr Tyr Asp Asp
1               5

<210> SEQ ID NO 20
<211> LENGTH: 13
<212> TYPE: PRT
<213> ORGANISM: HOMO SAPIENS

<400> SEQUENCE: 20

His Val Phe Pro His Asn His Thr Ala Asp Ile Gln Ser
1               5                   10

<210> SEQ ID NO 21
<211> LENGTH: 4
<212> TYPE: PRT
<213> ORGANISM: HOMO SAPIENS

<400> SEQUENCE: 21
```

Phe Ile Asn Phe
1

<210> SEQ ID NO 22
<211> LENGTH: 8
<212> TYPE: PRT
<213> ORGANISM: HOMO SAPIENS

<400> SEQUENCE: 22

Lys Glu Thr Lys Asp Gly Phe Met
1               5

<210> SEQ ID NO 23
<211> LENGTH: 441
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Gly Thr Thr Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu

```
                290                   295                   300
His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440
```

<210> SEQ ID NO 24
<211> LENGTH: 1323
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 24

```
caggttcagc tggtgcagtc tggtgctgag gtgaagaagc ctggtgcctc agtgaaggtc    60
tcctgcaagg cttctggtta cacattcact gactactaca tgcactgggt gcgtcaggcc   120
cctggtcaag tcttgagtg gatgggtcgt gttaatccta accggagggg tactacctac   180
aaccagaaat tcgagggccg tgtcaccatg accacagaca tccacgag cacagcctac   240
atggagctgc gtagcctgcg ttctgacgac acggccgtgt attactgtgc gcgtgcgaac   300
tggcttgact actggggcca gggcaccacc gtcaccgtct cctccgcctc caccaagggc   360
ccatcggtct tccccgctag cccctgctcc aggagcacct ccgagagcac agccgccctg   420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
agcagcgtgg tgaccgtgcc ctccagcagc ttgggcacga agacctacac ctgcaacgta   600
gatcacaagc ccagcaacac caaggtggac aagagagttg agtccaaata tggtccccca   660
tgcccaccct gcccagcacc tgaggccgcc ggggaccat cagtcttcct gttccccca   720
aaacccaagg acactctcat gatctcccgg acccctgagg tcacgtgcgt ggtggtggac   780
gtgagccagg aagaccccga ggtccagttc aactggtacg tggatggcgt ggaggtgcat   840
aatgccaaga caaagccgcg ggaggagcag ttcaacagca cgtaccgtgt ggtcagcgtc   900
ctcaccgtcc tgcaccagga ctggctgaac ggcaaggagt acaagtgcaa ggtctccaac   960
aaaggcctcc cgtcctccat cgagaaaacc atctccaaag ccaaggggca gccccgagag  1020
ccacaggtgt acaccctgcc cccatcccag gaggagatga ccaagaacca ggtcagcctg  1080
acctgcctgg tcaaaggctt ctaccccagc gacatcgccg tggagtggga aagcaatggg  1140
cagccggaga acaactacaa gaccacgcct cccgtgctgg actccgacgg ctccttcttc  1200
```

-continued

```
ctctacagca ggctaaccgt ggacaagagc aggtggcagg aggggaatgt cttctcatgc    1260
tccgtgatgc atgaggctct gcacaaccac tacacacaga agagcctctc cctgtctctg    1320
ggt                                                                  1323
```

MET ANTIBODY DRUG CONJUGATES

The present invention provides an antibody drug conjugate (ADC) having an IgG4 antibody that binds to MET conjugated to a cytotoxic agent, methods for their production, pharmaceutical compositions containing the MET ADCs, and uses thereof to treat various cancers.

The general concept for ADCs is well known and aims to take advantage of the specificity of monoclonal antibodies (mAbs) to deliver potent cytotoxic drugs selectively to antigen-expressing tumor cells. Despite the well-known concept, various aspects of an ADC must be carefully selected to fully realize the goal of a targeted therapy with improved efficacy and tolerability, including an appropriate antigen target, an appropriate antibody that binds that antigen target, the cytotoxic payload, a linker, the conjugation method, and the release mechanism. Despite advancements over the past several decades it is generally recognized that even skilled artisans frequently encounter significant problems associated with chemical and physical stability of ADCs which result in ineffective or even toxic compounds. For example, gemtuzamab ozogamicin (previously marketed as Mylotarg), is an anti-CD33 ADC that was approved by the FDA in May 2000 to treat acute myelogenous leukemia. However, it was subsequently withdrawn from the market in June 2010 when clinical trials revealed hepatotoxicity, fatal complications in certain groups of patients, increased patient death and no added efficacy benefit over conventional cancer therapies. ADCs may have significantly shorter elimination half-lives as compared to the parental antibodies themselves. Amino acid changes may be required in order to sufficiently overcome these problems. The antibody, linker and drug must often be modified to produce a targeted ADC therapy with improved efficacy and tolerability. Further, the structural changes that are required to reduce, eliminate, and/or avoid such properties are most often not routine or derived from common general knowledge.

MET, a member of the tyrosine kinase superfamily, is the human receptor for human hepatocyte growth factor (HGF). HGF is the sole ligand that binds to MET. Binding of HGF to MET leads to receptor dimerization or multimerization, phosphorylation of multiple tyrosine residues in the intracellular region, catalytic activation, and downstream signaling. Activation of the HGF/MET pathway is believed to be important in normal processes in embryonic development, cellular proliferation, migration, morphogenesis, survival and wound healing, but its dysregulation is believed to play a role in cancer development, metastasis, and drug resistance. MET is also activated via ligand-independent mechanisms, including receptor over-expression, amplification, and mutation. HGF and MET have also been targets for anti-cancer therapy. For example, onartuzumab, also known in the art as one-armed 5D5, OA5D5 or MetMAb, is a humanized, monovalent, antagonistic anti-MET antibody derived from the MET agonistic monoclonal antibody 5D5 (see, for example, Spigel, D. R., et al., (2013) Randomized Phase II Trial of Onartuzumab in Combination With Erlotinib in Patients With Advanced Non Small-Cell Lung Cancer, J. Clinical Oncology, 2013; 31(32):4105-4114; and Xiang H., et al., Onartuzumab (MetMAb): Using Nonclinical Pharmacokinetic and Concentration—Effect Data to Support Clinical Development, *Clin Cancer Res.* 19(18): 5068-5078 (2013)). Onartuzumab binds to MET and remains on the cell surface with MET, preventing HGF binding and subsequent MET phosphorylation as well as downstream signaling activity and cellular responses. Despite early excitement about the potential of onartuzumab in treating cancer, development of onartuzumab was eventually terminated due to a lack of clinically meaningful efficacy in a late stage clinical trial (see, e.g., Spigel, D. R., et al., Onartuzumab plus erlotinib versus erlotinib in previously treated stage IIIb and IV NSCLC: results from the pivotal phase III randomized, multicenter, placebo-controlled METLung (OAM4971g) global trial. J Clin Oncol., 32, abstr 8000 (2014)). Likewise, both Amgen and Aveo Oncology terminated all clinical development of their HGF antibodies, ficlatuzumab (formerly known as AV-299) and rilotumumab (formerly known as AMG102), respectively, both of which bound to the HGF ligand with high affinity and specificity to inhibit HGF/c-Met biological activities. More specifically, Aveo Oncology reported that patients positive for both vascular endothelial growth factor (VEGF) signaling pathway and epidermal growth factor receptor (EGFR) mutations experienced higher discontinuation rates, prompting the termination of the development of ficlatuzumab. Reportedly, Amgen's decision to terminate development of rilotumumab was based on a finding of an increase in the number of deaths in rilotumumab and chemotherapy treatment arms when compared to the chemotherapy treatment only arm (see, e.g., Cunningham, D., et al., Phase III, randomized, double-blind, multicenter, placebo (P)-controlled trial of rilotumumab plus epirubicin, cisplatin and capecitabine as first-line therapy in patients with advanced MET-positive gastric or gastroesophageal junction (G/GEJ) cancer: RILOMET-1 study. *J Clin Oncol.*, 33:(suppl; abstr 4000) (2015)).

WO 2010/059654 describes various MET antibodies including high-affinity antagonistic antibodies that bind to an epitope within the α-chain of MET and which induce internalization and/or degradation of MET in the presence or absence of HGF and in tumors characterized by mutations which confer resistance to known MET antagonists. One of the MET antibodies disclosed in WO 2010/059654, LY2875358, has been reported to have no functional (i.e., negligible) agonist activity on MET (see, for example, Zeng, W., et al., (2013) 104th AACR Annual Meeting, poster #5465). This antibody has been studied in clinical trials for advanced gastric cancer and non-small-cell lung cancer (NSCLC). Its World Health Organization (WHO) recommended International Non-Proprietary Name (INN) is emibetuzumab. WHO Drug Information, Vol. 29, No. 1, 2015, pp. 82-83.

WO 2016094455 and Fu, Y. et al., (2014) disclose an ADC having an IgG1 antibody that binds to MET conjugated at interchain cysteine sites with the tubulin inhibitor DM1 or a doxorubicin analog (Fu, Y., et al., c-Met is a Potential Therapeutic Target for Antibody Drug Conjugates in Breast Cancer, 37th Annual San Antonio Breast Cancer Symposium (poster # P2-16-03) (2014)).

As is well known in the art, "[p]hysical and chemical ADC, linker payload, and mAb instability could potentially impact the toxicity, immunogenicity, and efficacy of the molecule (Ross, P. L., and Wolfe, J. L., Physical and Chemical Stability of Antibody Drug Conjugates: Current Status, J. of Pharmaceutical Sciences, 105:391-397 (2016))." Indeed, when attempting to create MET ADCs comprising various anti-MET antibodies of WO 2010/059654 by generally following the teachings in the art (e.g., "Antibody-Drug Conjugates" (2013) Springer. Ducry, Laurent (Ed.), the present inventors encountered significant problems associated with the formation of half mAbs which may exchange with endogenous human IgG4 or increased agonist properties with respect to the target receptor, MET. Indeed, an extensive engineering effort involving different antibodies, payloads, linkers, and/or conjugation strategies was required either to avoid or sufficiently overcome these problems. The need for structural changes, as well as the actual changes required to overcome these problems, are not suggested in the relevant art. Further, several changes are not routine or derived from common general knowledge and the results of the structural engineering were surprising and advantageous. Thus, an extensive research effort lead to the identification of novel conjugation processes, payload intermediates, and surprisingly stable, well-tolerated, and efficacious MET ADCs.

Accordingly, the present invention provides ADCs that bind MET with high affinity and effectively neutralize MET activation by HGF. Additionally, the MET ADCs enable co-localization of MET antibody and a cytotoxic agent (i.e., MMAE) on the cell surface and effective release of the cytotoxic agent while eliciting minimal or no functional MET agonist activity. Surprisingly, these MET ADCs exhibit at least comparable ability to induce internalization and degradation of MET compared with the unconjugated, parental antibody, emibetuzumab, in tumor cells with MET expression. Furthermore, the MET ADCs provided herein exhibit increased efficacy in treating MET expressing tumors (relative to single-agents and/or combinations of single agents) including hard to treat cancers (e.g., lung, gastric, ovarian, prostate, thyroid, pancreatic, colorectal, and renal cancer), those characterized by having RAS activation (e.g., one or more KRAS mutations), low MET expressing tumors or tumors which are resistant, or have become resistant, to one or more anti-MET antibodies and/or one or more small molecule inhibitors of MET including, but not limited to, merestinib, as compared to relevant combinations of single-agents. Additionally, the MET ADCs provided herein are very stable in circulation, demonstrate in vivo stability, physical and chemical stability including, but not limited to, thermal stability, solubility, low self-association, and pharmacokinetic characteristics which are acceptable for development and/or use of the ADC in the treatment of cancer. Surprisingly, they also appear to have physical and chemical stability properties that are comparable to that of emibetuzumab.

The present invention provides a compound of formula I wherein A is an IgG4 antibody that binds MET and comprises:

i) a heavy chain comprising heavy chain complementarity determining regions (CDRs) HCDR1, HCDR2, and HCDR3 consisting of the amino acid sequences of GYTFTDYYMH (SEQ ID NO: 1), RVNPNRRGT-TYNQKFEG (SEQ ID NO: 2), and ARANWLDY (SEQ ID NO: 3), respectively; and ii) a light chain comprising light chain CDRs LCDR1, LCDR2, and LCDR3 consisting of the amino acid sequences of SVSSSVSSIYLH (SEQ ID NO: 4), YST-SNLAS (SEQ ID NO: 5) and QVYSGYPLT (SEQ ID NO: 6), respectively; and wherein n is 1 to 9; or a pharmaceutically acceptable salt thereof.

Formula 1

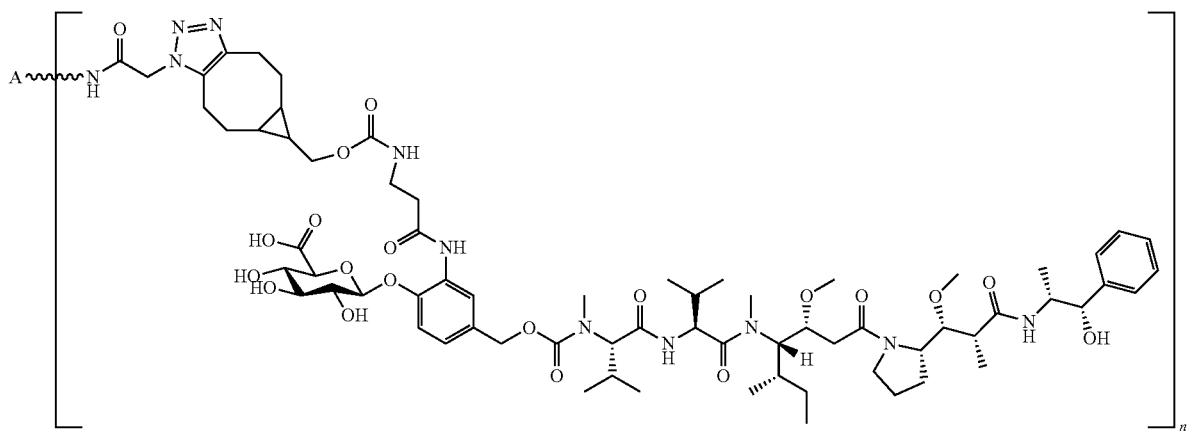

Another embodiment of the present invention provides a compound of formula I wherein A is an IgG4 antibody that binds MET and comprises:

(a) a first heavy chain comprising the amino acid sequence of SEQ ID NO: 23, and
(b) a first light chain comprising the amino acid sequence of SEQ ID NO: 9, and wherein n is 1 to 9; or a pharmaceutically acceptable salt thereof.

Another embodiment of the present invention provides a compound of formula I, wherein A is an IgG4 antibody that binds MET and comprises:

i) a first heavy chain and a second heavy chain wherein each of the heavy chains comprises heavy chain CDRs HCDR1, HCDR2, and HCDR3 consisting of the amino acid sequences of GYTFTDYYMH (SEQ ID NO: 1), RVNPNRRGTTYNQKFEG (SEQ ID NO: 2), and ARANWLDY (SEQ ID NO: 3), respectively; and ii) a first light chain and a second light chain wherein each of the light chains comprises light chain CDRs LCDR1, LCDR2, and LCDR3 consisting of the amino acid sequences of SVSSSVSSIYLH (SEQ ID NO: 4), YST-SNLAS (SEQ ID NO: 5) and QVYSGYPLT (SEQ ID NO: 6), respectively; and wherein n is 1 to 9; or a pharmaceutically acceptable salt thereof.

Another embodiment of the present invention provides a compound of formula I, wherein A is an IgG4 antibody that binds MET and comprises:

i) a first heavy chain and a second heavy chain wherein each of the heavy chains comprises a heavy chain variable region (HCVR) comprising the amino acid sequence of SEQ ID NO: 7; and ii) a first light chain and a second light chain wherein each of the light chains comprises a light chain variable region (LCVR) comprising the amino acid sequence of SEQ ID NO: 8; and wherein n is 1 to 9; or a pharmaceutically acceptable salt thereof.

Another embodiment of the present invention provides a compound of formula I, wherein A is an IgG4 antibody that binds MET and comprises:

i) a first heavy chain comprising the amino acid sequence of SEQ ID NO: 23; and ii) a first light chain comprising the amino acid sequence of SEQ ID NO:9, and wherein n is 1 to 9; or a pharmaceutically acceptable salt thereof.

Another embodiment of the present invention provides a compound of formula I, wherein A is an IgG4 antibody that binds MET and comprises:

i) a first heavy chain and a second heavy chain wherein each of the heavy chains comprises the amino acid sequence of SEQ ID NO: 23; and ii) a first light chain and a second light chain wherein each of the light chains comprises the amino acid sequence of SEQ ID NO: 9, and n is 1 to 9; or a pharmaceutically acceptable salt thereof.

Another embodiment of the present invention provides a compound of formula I, wherein A is an IgG4 antibody that binds MET and comprises (i) two heavy chain (HC) polypeptides and two light chain (LC) polypeptides wherein the amino acid sequence of both HC polypeptides consists of the amino acid sequence of SEQ ID NO: 23 and the amino acid sequence of both LC polypeptides consists of the amino acid sequence of SEQ ID NO: 9 both second polypeptides comprise the amino acid sequence of SEQ ID NO: 9, and n is 1 to 9; or a pharmaceutically acceptable salt thereof.

Further, the present invention provides a compound of formula I, or a pharmaceutically acceptable salt thereof, wherein A is C8-H241-IgG4 or emibetuzumab.

of formula I compounds may be characterized as a distribution represented by the term "drug to antibody ratio" (i.e., DAR).

A DAR value may be calculated by first determining the drug load distribution for each compound of formula I where n is 1 to 9. This may be achieved by using analytical techniques known in the field such as spectrophotometric assays, radiometric methods, hydrophobic interaction chromatography, and mass spectrometric methods. More specifically, a deconvoluted mass spectrum by Electrospray Ionization Time-of-Flight Mass Spectrometry (ESI-ToF) is obtained for the mixture. Individual peaks for each n value are integrated based on ion count. The ion count for each n value is divided by the sum of all peaks ion count and then multiplied by 100% to provide the drug load distribution.

Drug load distribution (%)=(ion count of compound of formula I where n is 1 to 9 divided by sum of ion count) times 100(%). The calculation is repeated for each peak representing a specific n value.

Next, the drug load distribution (%) of each compound of formula I where n is 1 to 9 is multiplied by its corresponding value n and the resulting product divided by 100. The resulting quotient represents the weighted DAR contribution of each compound of formula I with specific n value to the mixture profile. Finally, the sum of the DAR contribution provides the average DAR for the mixture.

DAR contribution=(drug load distribution (%) of each compound of formula I with a specific $n$ value)×($n$)/100.

Average DAR=Σ(DAR contribution).

The present invention provides a composition comprising a mixture of formula I compounds where the average DAR is 2 to 6.

Further the present invention provides a composition where the average DAR is 2 to 5.

Further the present invention provides a composition where the average DAR is 3 to 4.

Further the present invention provides a composition where the average DAR is 3.3.

A particular compound of formula I is

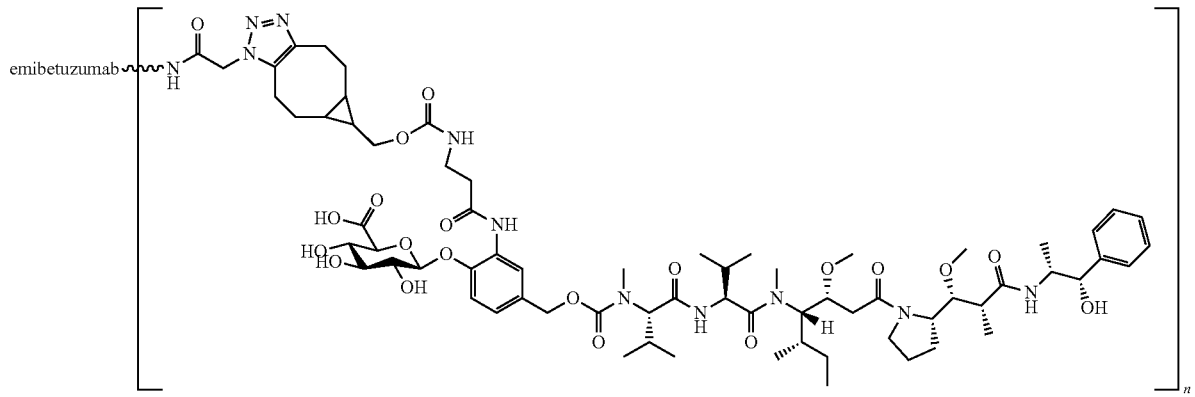

Further, the present invention provides a compound of formula I, or a pharmaceutically acceptable salt thereof, wherein n is 1 to 9.

In addition to a compound of formula I where n is 1 to 9, the present invention provides a composition comprising a mixture of formula I compounds where n is 1 to 9. A mixture wherein n is 1 to 9 or a pharmaceutically acceptable salt thereof.

Another embodiment of the present invention is a pharmaceutical composition, comprising any one of the foregoing MET ADCs, or a salt thereof, and a pharmaceutically acceptable carrier, diluent, or excipient.

Another embodiment of the present invention is any one of the foregoing MET ADCs, or a salt thereof, for use in therapy.

Another embodiment of the present invention is any one of the foregoing MET ADCs, or a salt thereof, for use in treating a cancer.

Another embodiment of the present invention is any one of the foregoing MET ADCs, or a salt thereof, for use in treating a cancer wherein MET is expressed by the patient's tumor.

Another embodiment of the present invention is any one of the foregoing MET ADCs, or salt thereof, for use in treating i) a cancer wherein MET is expressed by the patient's tumor at a low, moderate, or high level and/or ii) a tumor harboring one or more RAS (including, but not limited to, KRAS), BRAF, P53, and/or PI3K mutations. In various embodiments of such an invention, the use of a MET ADC for treating a cancer wherein MET is expressed by the patient's tumor at a low, moderate, or high level and/or a tumor which harbors one or more RAS (including, but not limited to, KRAS) BRAF, P53, and/or PI3K mutations may further comprise a step of identifying the patient in need of the treatment of the cancer, prior to the step of administering the MET ADC of the present invention, or salt thereof, to the patient.

Another embodiment of the present invention is any one of the foregoing MET ADCs, or a salt thereof, for use in treating pancreatic, ovary, prostate, gastric, colorectal, esophageal, liver, bladder, renal, renal papillary, thyroid, cervical, head and neck, and lung cancers, including, but not limited to, NSCLC and SCLC, as well as cholangiocarcinoma, or melanoma, including, but not limited to, uveal melanoma.

Another embodiment of the present invention is a method of treating a cancer, comprising administering to a human patient in need thereof an effective amount of any one of the foregoing MET ADCs, or a salt thereof.

Further, the present invention provides a method of treating pancreatic cancer comprising administrating to a patient in need thereof an effective amount of a compound of formula I or a salt thereof.

Further, the present invention provides a compound of formula I or salt thereof for use in the treatment of colorectal cancer.

Further, the present invention provides a compound of formula I or salt thereof for use in treating cancer.

Further, the present invention provides a compound of formula I or salt thereof for use in treating pancreatic cancer.

Further, the present invention provides certain intermediate compounds useful in the preparation of a compound of formula I. A particular intermediate compound is a compound of formula II.

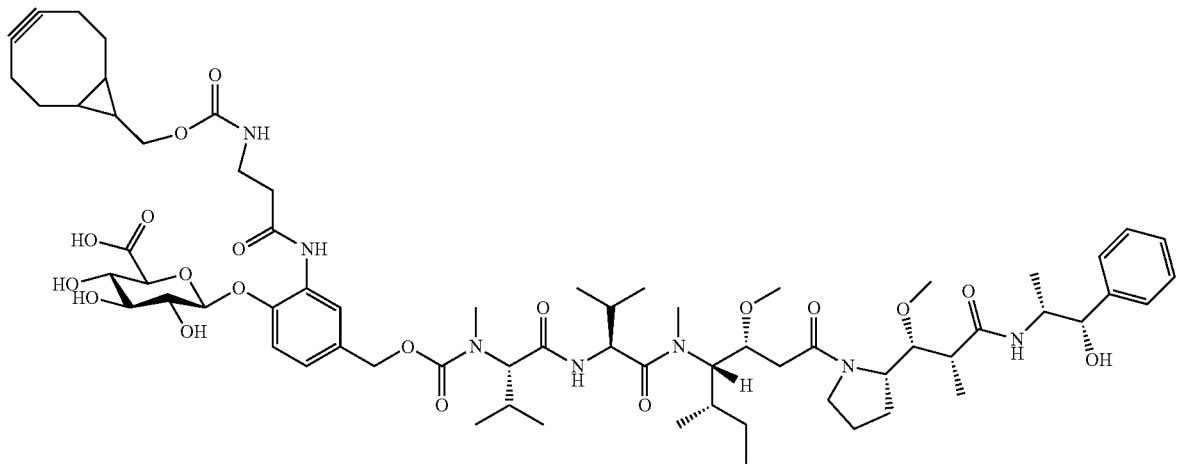

It is understood that compounds of the present invention may exist as stereoisomers. Embodiments of the present invention include all enantiomers, diastereomers, and mixtures thereof. Preferred embodiments are single diastereomers, and more preferred embodiments are single enantiomers. As such, it is understood within a compound of formula I is a compound of formula Ia.

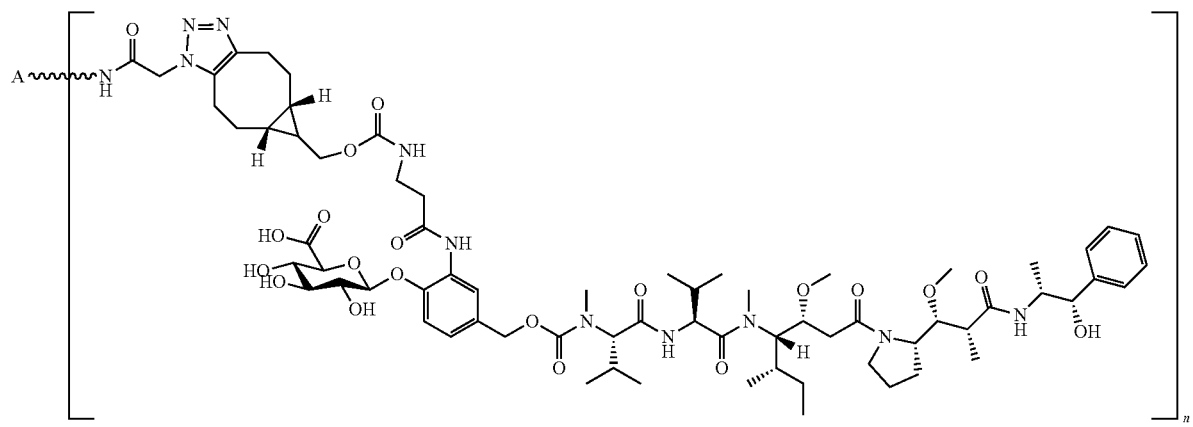

Further, it is understood that within a compound of formula II is a compound of formula IIa.

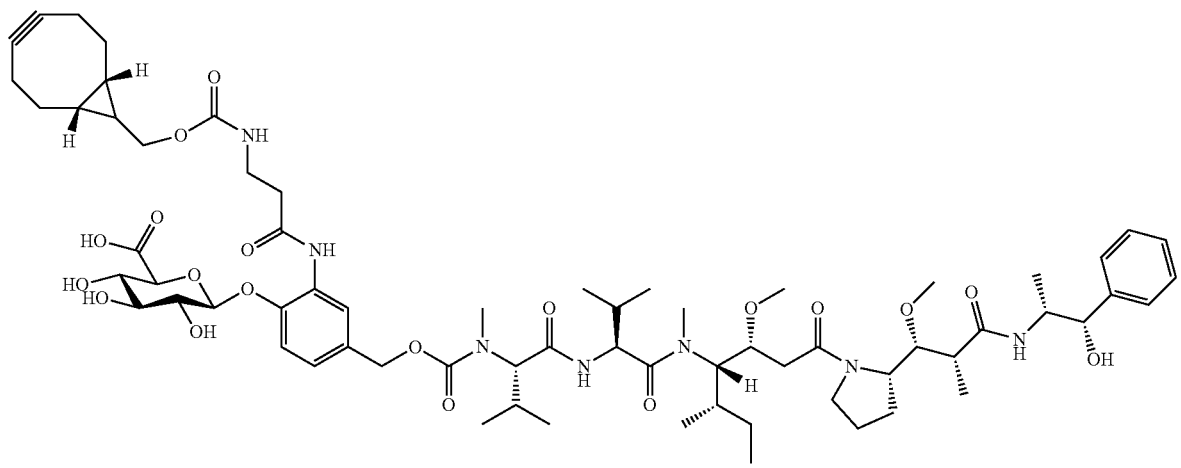

FIG. 1 depicts the results of competitive binding of MET-ADC #1 and emibetuzumab to cell surface MET on HT-29 tumor cells versus Alexa 488-labeled emibetuzumab. As clearly shown, MET-ADC #1 binding is highly comparable to the binding of unconjugated, parental MET antibody, emibetuzumab. Binding to cell surface MET was determined by FACS analysis.

Figure 1:
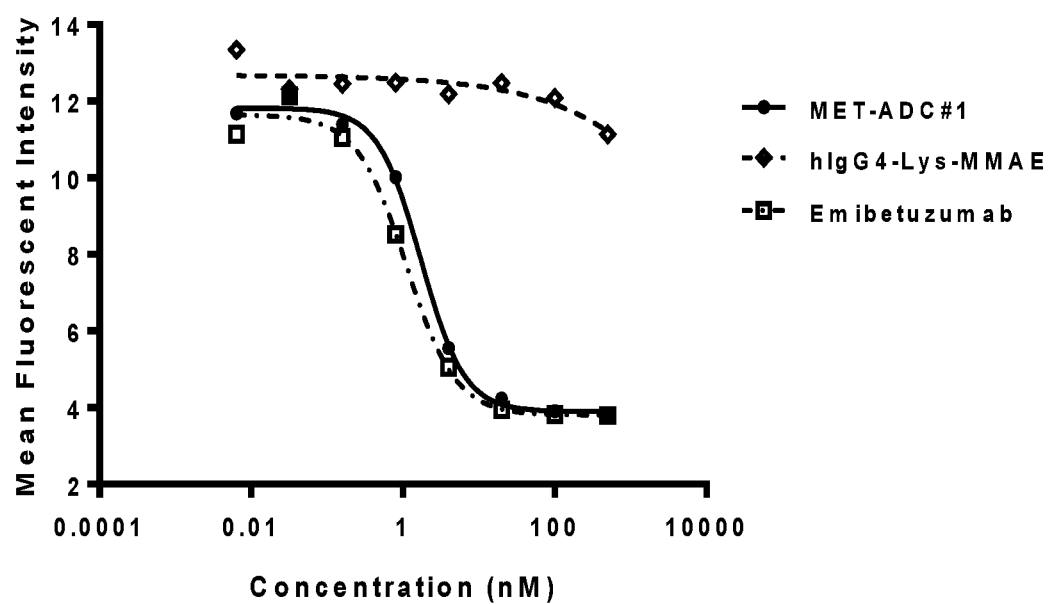

The terms "MET receptor" and "MET" are used interchangeably herein and, unless otherwise indicated, are intended to refer to the human receptor tyrosine kinase, as well as functionally active, mutated forms thereof, that bind human hepatocyte growth factor. Specific examples of MET include, e.g., a human polypeptide encoded by the nucleotide sequence provided in GenBank accession no. NM_000245, or the human protein encoded by the polypeptide sequence provided in GenBank accession no. NP_000236. MET is oftentimes referred to in the art by other names including, but not limited to, c-MET, cMET, c-Met, or other variations thereof. The structure of MET is depicted schematically as:

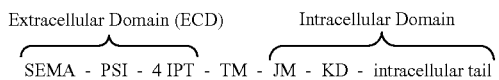

SEMA: Sema domain
PSI: Plexin, Semaphorins, and Integrins domain
IPT: 4 Immunoglobulins, Plexins, and Transcription factor domains
TM: Transmembrane region
JM: Juxtamembrane domain
KD: Kinase domain The extracellular domain of human MET has the amino acid sequence shown in, for example, SEQ ID NO: 11. However, amino acids 1-24 of SEQ ID NO: 11 comprise the signal sequence. Therefore, unless stated otherwise, the term "MET-ECD" as used herein means the mature protein beginning and ending at amino acids 25 and 932, respectively, of SEQ ID NO: 11 (i.e., SEQ ID NO: 12). The SEMA domain consists of approximately 500 amino acid residues at the N-terminus of MET, and contains the α-chain (amino acid residues 25-307 of SEQ ID NO: 11 (i.e., SEQ ID NO: 13) and part of the β-chain (amino acid residues 308-519 of SEQ ID NO: 11 (i.e., SEQ ID NO: 14)).

As used herein, the terms "low", "moderate", and "high" in reference to the cell surface expression of MET for a tumor or a cell line is intended to mean less than about 0.1 million, greater than about 0.1 million, and greater than about 0.5 million receptors per cell, respectively.

Unless indicated otherwise, the term "antibody", as used herein, is intended to refer to an immunoglobulin molecule comprising two heavy chains (HC) and two light chains (LC) interconnected by disulfide bonds. The amino terminal portion of each chain includes a variable region of about 100 to about 120 amino acids primarily responsible for antigen recognition via the CDRs contained therein. The carboxy-terminal portion of each chain defines a constant region primarily responsible for effector function.

As used herein, the term "C8-H241-IgG4" refers to an antibody comprising: two light chains, each of which has an amino acid sequence as in SEQ ID NO: 9, and two heavy chains, each of which has an amino acid sequence as in SEQ ID NO: 23.

As used herein, the term "emibetuzumab" refers to an antibody comprising: two light chains, each of which has an amino acid sequence as in SEQ ID NO: 9, and two heavy chains, each of which has an amino acid sequence as in SEQ ID NO: 23 and which is described in WHO Drug Information, *Proposed International Nonproprietary Names (INN) List* 111, Volume 28, No. 2, July 2014.

The term "complementarity determining region" and "CDR" as used herein is intended to mean the non-contiguous antigen combining sites found within the variable region of both HC and LC polypeptides of an antibody. These particular regions have been described by others including Kabat, et al., *Ann. NY Acad. Sci.* 190:382-93 (1971); Kabat et al., J. Biol. Chem. 252:6609-6616 (1977); Kabat, et al., *Sequences of Proteins of Immunological Interest*, Fifth Edition, U.S. Department of Health and Human Services, NIH Publication No. 91-3242 (1991); Chothia, et al., J. Mol. Biol. 196:901-917 (1987); MacCallum, et al., J. Mol. Biol., 262: 732-745 (1996); and North, et al., J. Mol. Biol., 406, 228-256 (2011) where the definitions include overlapping or subsets of amino acid residues when compared against each other.

The CDRs are interspersed with regions that are more conserved, termed framework regions ("FR"). Each LCVR and HCVR is composed of three CDRs and four FRs, arranged from amino-terminus to carboxy-terminus in the following order: FR1, CDR1, FR2, CDR2, FR3, CDR3, FR4. The three CDRs of the light chain are referred to as "LCDR1, LCDR2, and LCDR3" and the three CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions is in accordance with known conventions (e.g., Kabat (1991) Chothia (1987), and/or North (2011)).

The term "pharmaceutically acceptable salt" includes a base addition salt that exists in conjunction with an acidic portion of the molecule or an acid addition salt that exists in conjunction with the basic portion of a compound of formula I. Such salts include the pharmaceutically acceptable salts, for example those listed in Handbook of Pharmaceutical Salts: Properties, Selection and Use, P. H. Stahl and C. G. Wermuth (Eds.), Wiley-VCH, New York, 2002 which are known to the skilled artisan.

In addition to pharmaceutically acceptable salts, other salts are contemplated in the invention. They may serve as intermediates in the purification of compounds or in the preparation of other pharmaceutically-acceptable salts, or are useful for identification, characterization or purification of compounds of the invention.

As used herein, the term "patient" refers to an animal such as a mammal and includes a human. A human is a preferred patient.

It is also recognized that one skilled in the art may treat susceptible cancers by administering to a patient presently displaying symptoms an effective amount of the compound of formula I. Thus, the term "treating" (or "treat", or "treatment" are intended to refer to all processes wherein there may be a slowing, interrupting, arresting, controlling, or stopping of the progression of an existing disorder and/or symptoms thereof, but does not necessarily indicate a total elimination of all symptoms.

The term "surface plasmon resonance (SPR)", as used herein, refers to an optical phenomenon that allows for the analysis of real-time interactions by detection of alterations in protein concentrations within a biosensor matrix, for example using the BIAcore™ system (Biacore Life Sciences Division, GE Healthcare, Piscataway, N.J.).

The term "$K_D$", as used herein, is intended to refer to the equilibrium dissociation constant of a particular antibody-antigen or antibody fragment-antigen interaction.

The term "binds," or the like, means that an antibody or antigen-binding fragment thereof forms a complex with an antigen that is relatively stable under physiologic conditions. Methods for determining whether an antibody binds to an antigen are well known in the art and include, for example, SPR (see, Example 6, herein), or competitive binding assays against the antigen's (i.e., MET) natural ligand (i.e., HGF) or competitive binding assay against the parental antibody (emibetuzumab) and MET ADC (see, Example 8, herein), and the like. For example, an antibody that "binds" MET, as used in the context of the present invention, includes antibodies that bind MET-ECD (or the SEMA domain or the α-chain portions thereof) with a $K_D$ of less than about 10 nM, less than about 5 nM, less than about 4 nM, less than about 3 nM, less than about 2 nM, less than about 1 nM, less than about 0.5 nM, less than about 0.3 nM, less than about 0.2 nM, or less than about 0.1 nM as measured in a SPR assay (see, e.g., Example 6, herein). Preferably, a MET ADC of the present invention binds MET-ECD (or the SEMA domain or the α-chain portions thereof) with a $K_D$ of between about 50 nM and about 0.1 nM, between about 15 nM and about 0.1 nM, between about 15 nM and about 1.0 nM, between about 10 nM and about 1.0 nM, between about 7.5 nM and about 1.0 nM, between about 6 nM and about 1.0 nM, between about 3 nM and about 1.0 nM, between about 1 nM and about 0.1 nM, between about 0.75 nM and about 0.1 nM, between about 0.5 nM and about 0.1 nM as measured in a SPR assay designed to avoid or eliminate avidity effects on the affinity determinations (i.e., non-avidity binding) (see, e.g., Example 6, herein).

It is understood that within the chemical formula describing the present invention that the A wavy bond to nitrogen (N) represents a lysine residue of the group A where A is an IgG4 antibody that binds MET. As such, the present invention provides a compound of formula III useful in preparing a compound of formula I.

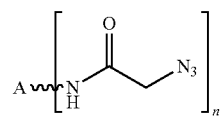

Where

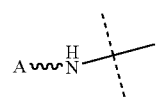

represents a functionized lysine residue of A.

An embodiment of the present invention provides a compound of formula I

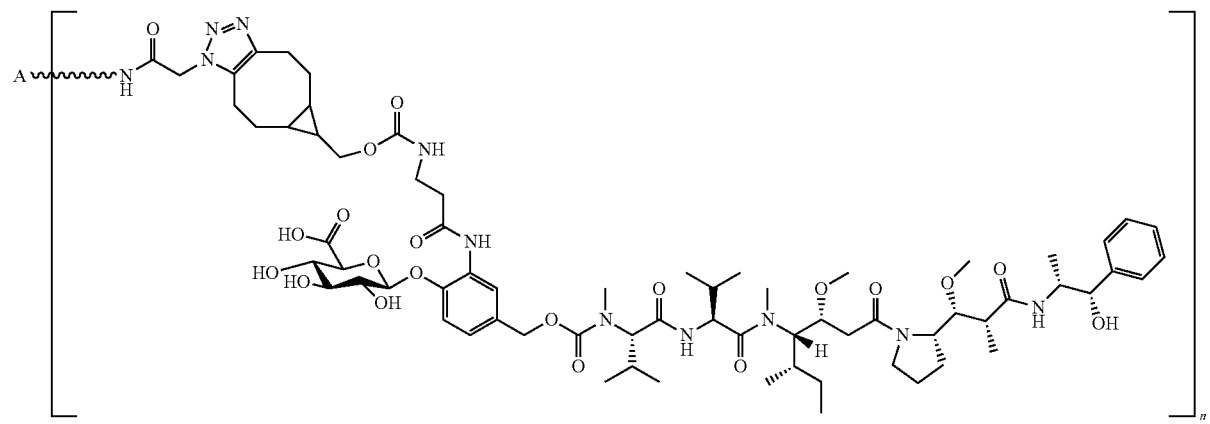

Formula 1 wherein
A is an IgG4 antibody that binds MET and comprises:
i) a heavy chain comprising heavy chain CDRs HCDR1, HCDR2, and HCDR3 consisting of the amino acid sequences of GYTFTDYYMH (SEQ ID NO: 1), RVNPNRRGTTYNQKFEG (SEQ ID NO: 2), and ARANWLDY (SEQ ID NO: 3), respectively; and
ii) a light chain comprising light chain CDRs LCDR1, LCDR2, and LCDR3 consisting of the amino acid sequences of SVSSSVSSIYLH (SEQ ID NO: 4), YSTSNLAS (SEQ ID NO: 5) and QVYSGYPLT (SEQ ID NO: 6), respectively; and
n is 1 to 9; or a pharmaceutically acceptable salt thereof.

Other embodiments of the present invention provide a compound of formula I,
wherein A is an IgG4 antibody that binds MET and comprises:
i) a heavy chain comprising the amino acid sequence of SEQ ID NO: 23; and
ii) a light chain comprising the amino acid sequence of SEQ ID NO: 9; and
n is 1 to 9; or a pharmaceutically acceptable salt thereof.

Another embodiment of the present invention is a compound of formula I

Formula 1

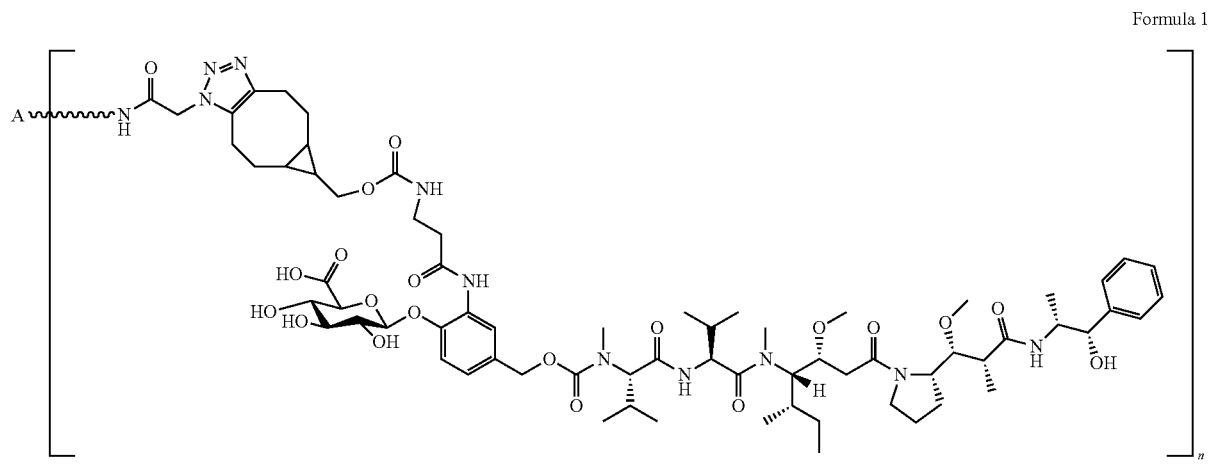

wherein

A is an IgG4 antibody that binds MET and comprises:

i) a first heavy chain and a second heavy chain wherein each of the heavy chains comprises heavy chain CDRs HCDR1, HCDR2, and HCDR3 consisting of the amino acid sequences of GYTFTDYYMH (SEQ ID NO: 1), RVNPNRRGTTYNQKFEG (SEQ ID NO: 2), and ARANWLDY (SEQ ID NO: 3), respectively; and ii) a first light chain and a second light chain wherein each of the light chains comprises light chain CDRs LCDR1, LCDR2, and LCDR3 consisting of the amino acid sequences of SVSSSVSSIYLH (SEQ ID NO: 4), YSTSNLAS (SEQ ID NO: 5) and QVYSGYPLT (SEQ ID NO: 6), respectively; and n is 1 to 9; or a pharmaceutically acceptable salt thereof. In other embodiments of such an invention A is an IgG4 antibody that binds MET and comprises:

i) a first heavy chain and a second heavy chain wherein both heavy chains comprise the amino acid sequence of SEQ ID NO: 23; and ii) a first light chain and a second light chain wherein both light chains comprise the amino acid sequence of SEQ ID NO:9. Furthermore, in various embodiments of such invention the MET ADC induces HGF-independent and EGF-independent internalization and/or degradation of cell surface MET.

In some embodiments of the MET ADC compounds disclosed herein, the heavy chain variable region amino acid sequence of SEQ ID NO: 7, and the light chain variable region amino acid sequence of SEQ ID NO: 8, which are both derived from the anti-MET Clone C8-H241 (which is described in detail in WO 2010/059654), can be used to form the antigen-binding sites of the MET antibody that binds to MET.

Another embodiment of the present invention is a MET ADC that binds MET comprising: (a) two first polypeptides wherein both of the first polypeptides comprise the amino acid sequence of SEQ ID NO: 23; and (b) two second polypeptides wherein both of the second polypeptides comprise the amino acid sequence of SEQ ID NO: 9.

Another embodiment of the present invention is a pharmaceutical composition comprising a MET ADC comprising: (a) two first polypeptides wherein both of the first polypeptides comprise the amino acid sequence of SEQ ID NO: 23; and (b) two second polypeptides wherein both of the second polypeptides comprise the amino acid sequence of SEQ ID NO: 9, and a pharmaceutically acceptable carrier, diluent, or excipient.

Another embodiment of the present invention is a method of treating cancer, comprising administering to a patient in need thereof an effective amount of a compound of formula I

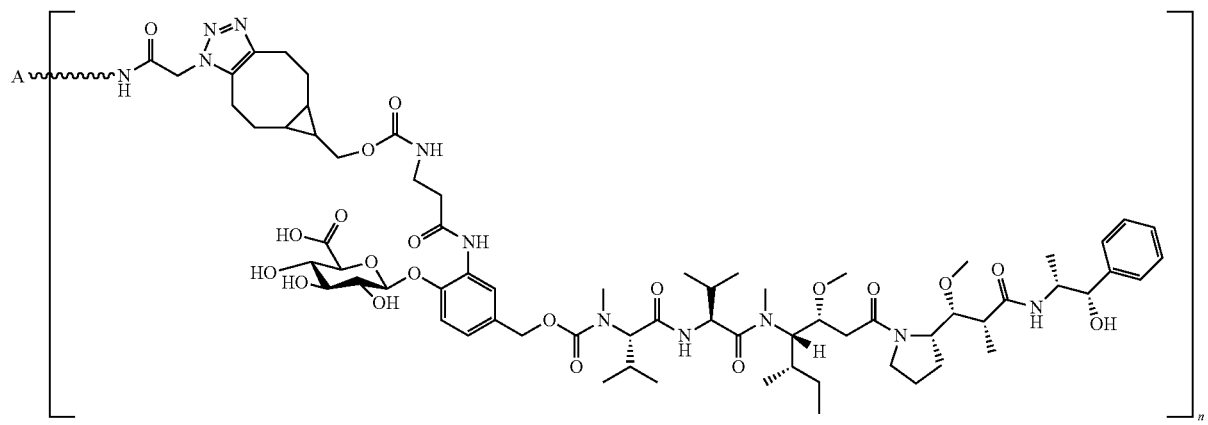

Formula 1 wherein
A is an IgG4 antibody that binds MET and comprises:
iii) a heavy chain comprising heavy chain CDRs HCDR1, HCDR2, and HCDR3 consisting of the amino acid sequences of GYTFTDYYMH (SEQ ID NO: 1), RVNPNRRGTTYNQKFEG (SEQ ID NO: 2), and ARANWLDY (SEQ ID NO: 3), respectively; and
iv) a light chain comprising light chain CDRs LCDR1, LCDR2, and LCDR3 consisting of the amino acid sequences of SVSSSVSSIYLH (SEQ ID NO: 4), YSTSNLAS (SEQ ID NO: 5) and QVYSGYPLT (SEQ ID NO: 6), respectively; and
n is 1 to 9; or a pharmaceutically acceptable salt thereof.

Another embodiment of the present invention is a method of treating cancer, comprising administering to a patient in need thereof an effective amount of a compound of formula I, wherein A is an IgG4 antibody that binds MET and comprises:
iii) a heavy chain comprising the amino acid sequence of SEQ ID NO: 23; and
iv) a light chain comprising the amino acid sequence of SEQ ID NO: 9; and
n is 1 to 9; or a pharmaceutically acceptable salt thereof.

Another embodiment of the present invention is a method of treating cancer, comprising administering to a patient in need thereof an effective amount of a compound of formula I

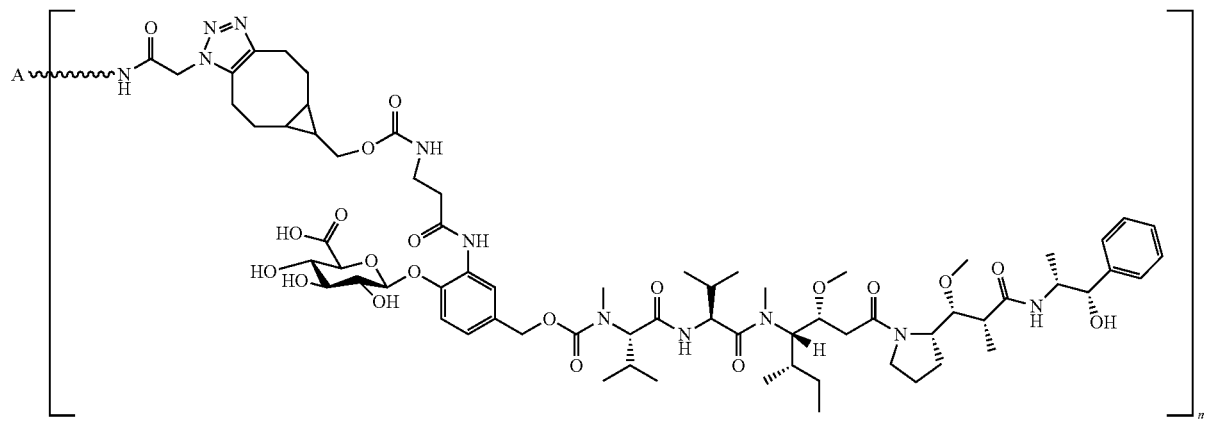

Formula 1 wherein
A is an IgG4 antibody that binds MET and comprises:
iii) a first heavy chain and a second heavy chain wherein each of the heavy chains comprise heavy chain CDRs HCDR1, HCDR2, and HCDR3 consisting of the amino acid sequences of GYTFTDYYMH (SEQ ID NO: 1), RVNPNRRGTTYNQKFEG (SEQ ID NO: 2), and ARANWLDY (SEQ ID NO: 3), respectively; and
iv) a first light chain and a second light chain wherein each of the light chains comprises light chain CDRs LCDR1, LCDR2, and LCDR3 consisting of the amino acid sequences of SVSSSVSSIYLH (SEQ ID NO: 4), YSTSNLAS (SEQ ID NO: 5) and QVYSGYPLT (SEQ ID NO: 6), respectively; and n is 1 to 9; or a pharmaceutically acceptable salt thereof. In other embodiments of such methods of treating cancer, A is an IgG4 antibody that binds MET and comprises:

iii) a first heavy chain and a second heavy chain wherein both heavy chains comprise the amino acid sequence of SEQ ID NO: 23; and iv) a first light chain and a second light chain wherein both light chains comprise the amino acid sequence of SEQ ID NO:9. Furthermore, in various embodiments of such methods of treating cancer the MET ADC induces HGF-independent internalization and/or degradation of cell surface MET.

In some embodiments of the methods of treating cancer disclosed herein, the heavy chain variable region amino acid sequence of SEQ ID NO: 7, and the light chain variable region amino acid sequence of SEQ ID NO: 8, which are both derived from the anti-MET Clone C8-H241 (which is described in detail in WO 2010/059654), can be used to form the antigen-binding sites of the MET antibody that binds to MET.

Another embodiment of the present invention is a method of treating cancer, comprising administering to a patient in need thereof an effective amount of a compound of formula I that binds MET and comprises: (a) two first polypeptides wherein both of the first polypeptides comprise the amino acid sequence of SEQ ID NO: 23; and (b) two second polypeptides wherein both of the second polypeptides comprise the amino acid sequence of SEQ ID NO: 9.

Another embodiment of the present invention is the use of a pharmaceutical composition comprising a MET ADC comprising: (a) two first polypeptides wherein both of the first polypeptides comprise the amino acid sequence of SEQ ID NO: 23; and (b) two second polypeptides wherein both of the second polypeptides comprise the amino acid sequence of SEQ ID NO: 9, and a pharmaceutically acceptable carrier, diluent, or excipient.

In some embodiments of the methods of treating cancer with at least one of the MET ADC compounds of the present invention, the cancer is pancreatic, ovary, prostate, gastric, colorectal, esophageal, liver, bladder, renal, renal papillary, thyroid, cervical, head and neck, and lung cancers, including, but not limited to, NSCLC and SCLC, as well as cholangiocarcinoma, or melanoma, including, but not limited to, uveal melanoma.

In some embodiments of the present invention, methods of treating cancer with at least one of the MET ADC compounds of the present invention, wherein the tumor is characterized by comprising cells having one or more KRAS mutations is provided. Other embodiments of the present invention also provide methods of treating a cancer, including administering a pharmaceutically effective amount of one of the foregoing MET ADCs, or a salt thereof, to a patient in need thereof wherein MET is expressed by the patient's tumor at a low, moderate, or high level and/or the tumor is resistant, or has become resistant, to one or more anti-MET antibodies (e.g., emibetuzumab, etc.) and/or one or more small molecule inhibitors of MET (e.g., Crizotinib, merestinib, etc.), including, but not limited to, tumors harboring KRAS mutations. In various embodiments of such an invention, the method of treating a cancer wherein MET is expressed by the patient's tumor at a low, moderate, or high level and/or wherein the tumor is resistant, or has become resistant, to one or more anti-MET antibodies (e.g., emibetuzumab, etc.) and/or one or more small molecule inhibitors of MET (e.g., Crizotinib, merestinib, etc.), including, but not limited to, tumors harboring KRAS mutations may further comprise a step of identifying the patient in need of the treatment of the cancer, prior to the step of administering the MET ADC, or a salt thereof, to the patient by measuring the levels of MET expressed by the patient's tumor and/or assessing whether the patient's tumor comprises cells having one or more KRAS mutations.

The MET antibody can be prepared by recombinant expression using techniques well-known in the art.

Although it is theoretically possible to express antibodies in either prokaryotic or eukaryotic host cells, eukaryotic cells are preferred, and most preferably mammalian host cells, because such cells are more likely to assemble and secrete a properly folded and immunologically active antibody. Preferred mammalian host cells for expressing the recombinant antibodies used of the invention include Chinese Hamster Ovary (CHO cells) [including dhfr minus CHO cells, as described in Urlaub and Chasin, *Proc. Natl. Acad. Sci. USA* 77:4216-20, 1980, used with a DHFR selectable marker, e.g., as described in Kaufman and Sharp, *J. Mol. Biol.* 159:601-21, 1982], NS0 myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown under appropriate conditions known in the art. Antibodies can be recovered from the host cell and/or the culture medium using standard purification methods.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification. Preferably, the heavy chain constant region is of an IgG type, and, more preferably, of a $IgG_4$ subtype.

An isolated DNA encoding a LCVR region may be converted to a full-length light chain gene (as well as to a Fab light chain gene) by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

The invention also provides any one of the foregoing MET ADCs, or a salt thereof, for use in therapy.

The invention also provides any one of the foregoing MET ADCs, or a salt thereof, for use in treating a cancer.

The invention also provides any one of the foregoing MET ADCs, or a salt thereof, for use in treating a cancer wherein MET is expressed.

The invention also provides any one of the foregoing MET ADCs, or a salt thereof, for use in treating pancreatic, ovary, prostate, gastric, colorectal, esophageal, liver, bladder, renal, renal papillary, thyroid, cervical, head and neck, and lung cancers, including, but not limited to, NSCLC and SCLC, as well as cholangiocarcinoma, or melanoma, including, but not limited to, uveal melanoma.

The invention also provides a method of treating a cancer, comprising administering to a human patient in need thereof an effective amount of any one of the foregoing MET ADCs, or a salt thereof.

The term "cancer" (or "a cancer") refers to proliferative diseases, such as lung cancer, non-small cell lung cancer (NSCLC), small cell lung cancer (SCLC), cancer of the head or neck, rectal cancer, cancer of the anal region, stomach cancer, gastric cancer, colon cancer, colorectal carcinoma (CRC), esophageal cancer, melanoma, including, but not limited to, uveal melanoma, liver cancer, cervical cancer, cancer of the bladder, cancer of the kidney or ureter, renal, renal papillary, thyroid cell carcinoma, carcinoma of the renal pelvis, including refractory versions of any of the above cancers, or a combination of one or more of the above cancers.

As used herein, the term "effective amount" refers to an amount, that is a dosage, which is effective in treating a disorder, such as colorectal cancer described herein. One skilled in the art, can readily determine an effective amount by the use of conventional techniques and by observing results obtained under analogous circumstances. In determining an effective amount or dose, a number of factors are considered, including, but not limited to, the compound to be administered; the co-administration of other agents, if used; the species of mammal; its size, age, and general health; the degree of involvement or the severity of the disorder, such as colorectal cancer; the response of the individual patient; the mode of administration; the bioavailability characteristics of the preparation administered; the dose regimen selected; the use of other concomitant medication; and other relevant circumstances. An effective amount is also one in which any detrimental effect(s) of the MET ADC, or salt thereof, are outweighed by the therapeutically beneficial effects.

An effective amount is at least the minimal amount, but less than an overall harmful amount, of an active agent which is necessary to impart therapeutic benefit to a subject. Stated another way, an effective amount or therapeutically effective amount of an antibody of the invention is an amount which in mammals, preferably humans, reduces the number of cancer cells; reduces the tumor size; inhibits (i.e., slow to some extent or stop) cancer cell infiltration into peripheral tissues organs; inhibit (i.e., slow to some extent or stop) tumor metastasis; inhibits, to some extent, tumor growth; and/or relieves to some extent one or more of the symptoms associated with the cancer. An effective amount of a MET ADC of the invention may be administered in a single dose or in multiple doses. Furthermore, an effective amount of a MET ADC of the invention may be administered in multiple doses of amounts that would be less than an effective amount if not administered more than once.

As is well known in the medical arts, dosages for any one subject depends upon many factors, including the patient's size, body surface area, age, the particular compound to be administered, gender, time and route of administration, general health, and other drugs being administered concurrently. Dose may further vary depending on the type and severity of the disease. A typical dose can be, for example, in the range of about 10 mg to about 1000 mg; preferably, about 50 mg to about 500 mg; more preferably, about 200 mg to about 500 mg; even more preferably, about 200 mg to about 400 mg, even more preferably, about 200 mg to about 300 mg; even more preferably, about 225 mg to about 275 mg; even more preferably, about 250 mg to about 275 mg; however, doses below or above this exemplary range are envisioned, especially considering the aforementioned factors. A daily parenteral dosage regimen can be from about 250 µg/kg to about 10 mg/kg. Progress may be monitored by periodic assessment, and the dose adjusted accordingly.

In some embodiments of the present invention, a single dose of a MET ADC of the present invention may be administered intravenously for treating a cancer in an adult patient. A typical single dose for intravenous administration can be, for example, in the range of about 10 mg to about 1000 mg; preferably, about 10 mg to about 500 mg; more preferably, about 10 mg to about 500 mg; more preferably, about 10 mg to about 400 mg; more preferably, about 10 mg to about 350 mg; more preferably, about 10 mg to about 300 mg; even more preferably, about 10 mg to about 275 mg; even more preferably, about 10 mg to about 250 mg; even more preferably, about 10 mg to about 200 mg; even more preferably, about 10 mg to about 175 mg; even more preferably, about 10 mg to about 150 mg; or most preferably, about 10 mg to about 125 mg; however, doses below or above this exemplary range are envisioned, especially considering the aforementioned factors. Alternatively, a typical single dose for intravenous administration of a MET ADC of the present invention can be, for example, from about 0.2 mg/kg to about 15 mg/kg body weight; more preferably, about 0.2 mg/kg to about 10 mg/kg; even more preferably, about 0.2 mg/kg to about 7.5 mg/kg; even more preferably, about 0.2 mg/kg to about 5 mg/kg; even more preferably, about 0.2 mg/kg to about 4 mg/kg; even more preferably, about 0.2 mg/kg to about 3 mg/kg; even more preferably about 0.2 mg/kg to about 2.5 mg/kg; or most preferably, about 0.2 mg/kg to about 2 mg/kg. Such doses can be administered intravenously once every week, once every two weeks, once every three weeks, or once every month, for example. Progress may be monitored by periodic assessment, and the dose adjusted accordingly.

These suggested amounts of a MET ADC of the present invention are subject to a great deal of therapeutic discretion. The key factor in selecting an appropriate dose and scheduling is the result obtained. Factors for consideration in this context include the particular disorder being treated, the clinical condition of the individual patient, the cause of the disorder, the site of delivery of the antibody, the particular type of antibody, the method of administration, the scheduling of administration, and other factors known to medical practitioners.

The MET ADCs of the present invention can be used as medicaments in human medicine, administered by a variety of routes. Accordingly, the invention also provides pharmaceutical compositions comprising any one of the foregoing MET ADCs, and a pharmaceutically acceptable carrier, diluent, or excipient. Most preferably, such compositions are for parenteral administration. The term parenteral as used herein includes intravenous, intramuscular, subcutaneous, or intraperitoneal administration. Parenteral delivery by intravenous or intraperitoneal or subcutaneous administration is preferred. Intravenous administration is most preferred. Suitable vehicles for such administration are well known in the art.

The pharmaceutical composition typically must be sterile and stable under the conditions of manufacture and storage in the container provided, including e.g., a sealed vial, syringe or other delivery device, e.g., a pen. Therefore, pharmaceutical compositions may be sterile filtered, or otherwise made free of microbial contamination, after making the formulation.

The ADCs of the present invention may be administered to a human subject alone or in the form of a pharmaceutical composition combined with pharmaceutically acceptable carriers, excipients, and/or diluents (the proportion, and nature of which are determined by the solubility and chemical properties, including stability) of the compound selected, the chosen route of administration, and standard pharmaceutical practice) in single or multiple doses. Such pharmaceutical compositions are designed to be appropriate for the selected mode of administration, and pharmaceutically acceptable diluents, carrier, and/or excipients such as dispersing agents, buffers, surfactants, preservatives, solubilizing agents, isotonicity agents including but not limited to sodium chloride, stabilizing agents and the like are used as appropriate. Said compositions can be designed in accordance with conventional techniques disclosed in, e.g., *Remington, The Science and Practice of Pharmacy*, L. V. Allen, Editor, 22$^{nd}$ Edition, Pharmaceutical Press (2012) which provides a compendium of formulation techniques as are generally known to practitioners. Suitable carriers for pharmaceutical compositions include any material which, when combined with an antibody of the invention, retains the molecule's activity and is non-reactive with the subject's immune system. The compounds of the present invention, while effective themselves, may also be formulated and administered in the form of their pharmaceutically acceptable salts for convenience of crystallization, increased solubility, and the like.

A compound of formula I may be prepared by processes known in the chemical arts or by a novel process described herein. A process for the preparation of a compound of formula I and novel intermediates for the manufacture of a compound of formula I, provide further features of the invention and are illustrated in the following procedures.

Generally, a compound of formula I wherein n is 1 to 9 may be prepared from a compound of formula II (Scheme 1). More specifically, a compound of formula II is reacted with a compound of formula III where n is 1 to 9 in a solvent such as phosphate buffered saline and DMSO to provide a compound of formula I.

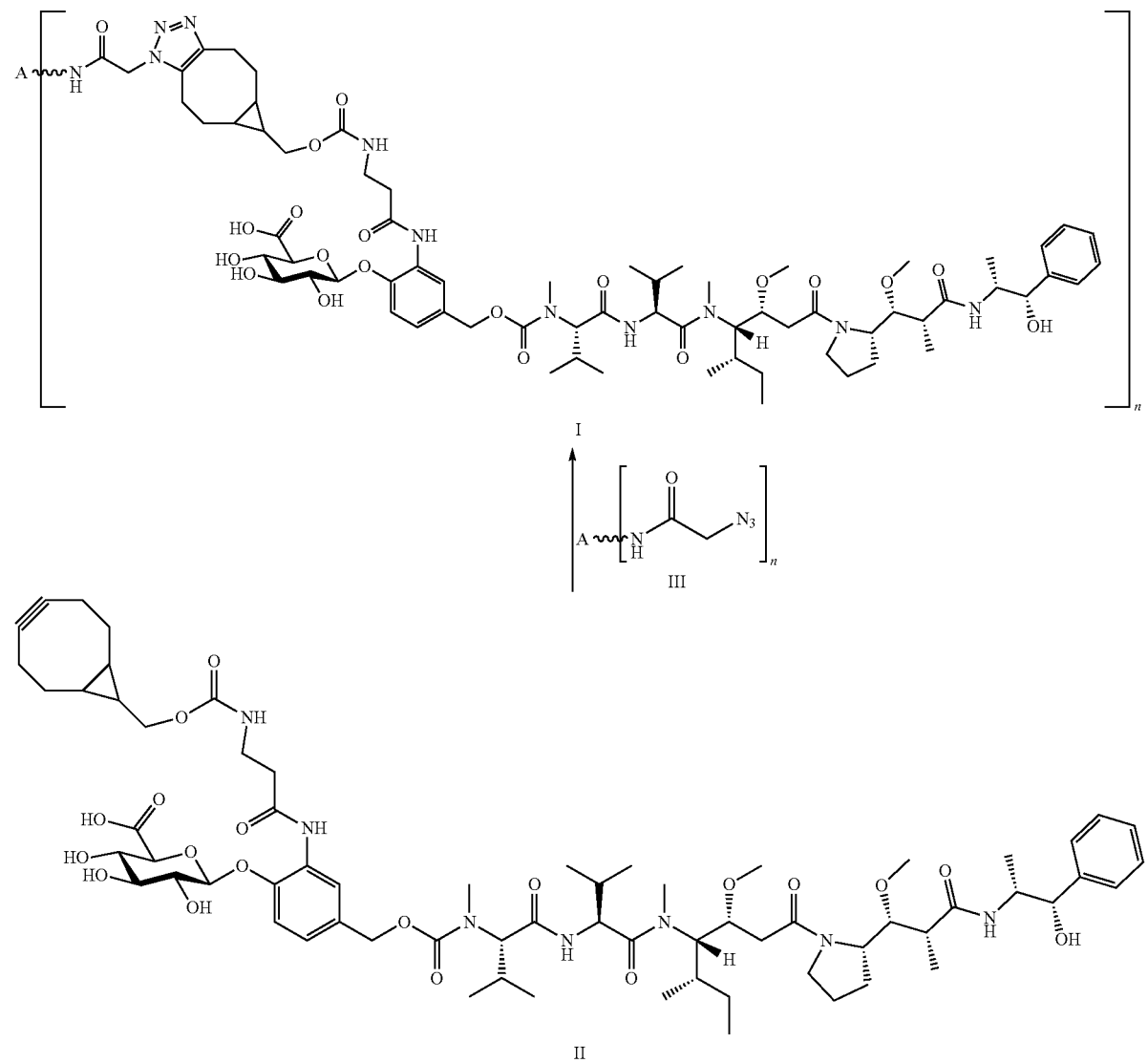

Scheme 1

Generally, a compound of formula III may be prepared by reacting a lysine group of a MET antibody formula IV) with (2,5-dioxopyrrolidin-1-yl) 2-azidoacetate (Scheme 2). More specifically, a compound of formula IV, A, which is a MET monoclonal antibody such as C8-H241-IgG4 or more specifically, emibetuzumab, is reacted with (2,5-dioxopyrrolidin-1-yl) 2-azidoacetate in a solvent such as phosphate buffered saline and DMSO to provide a compound of formula III where n, which represents the number of 2-azidoacetyl-lysine groups, is 1 to 9. A molar excess of (2,5-dioxopyrrolidin-1-yl) 2-azidoacetate to the amount of the formula IV compound of 11:1 to 5:1 is typically used. Preferably the molar ratio of (2,5-dioxopyrrolidin-1-yl) 2-azidoacetate to a compound of formula IV is about 9:1 to 6:1. More preferably, the molar ratio is about 7.75:1. The value of n and its contribution to the average drug antibody ratio (DAR) may be controlled in this step by modification of reaction conditions including the molar ratio of (2,5-dioxopyrrolidin-1-yl) 2-azidoacetate to a compound of formula IV as well as other standard techniques.

Generally, a compound of formula II may be prepared from a compound of formula V (Scheme 3). More specifically, a compound of formula V is reacted with (1R,9S,9S)-bicyclo[6.1.0]non-4-yl-9-yl-methyl (4-nitrophenyl)carbonate in the presence of a base such as diisopropylethylamine to provide a compound of formula II. The reaction is typically carried out in a solvent such as dimethylformamide. A compound of formula V may be prepared by first reacting a compound of formula VI with a compound of formula VII in the presence of a base such as diisopropylethylamine and an activating agent such as hydroxybenzotriazole. The reaction is typically carried out in a solvent such as dimethylformamide. The resulting coupled product is reacted with a base such as aqueous lithium hydroxide in a solvent such as methanol to provide a compound of formula V.

A compound of formula VI may be prepared as described in the Preparations and Examples. A compound of formula VII may be prepared by procedures appreciated by one of ordinary skill in the art including those disclosed in International Application Publication No. WO 2002/088172.

Scheme 2

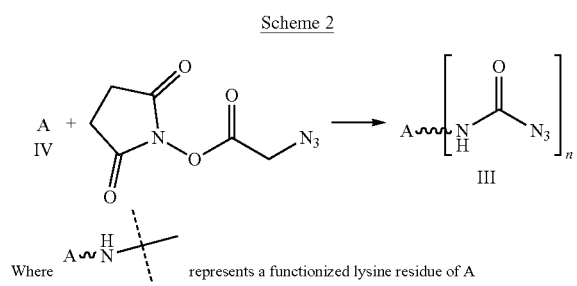

Scheme 3

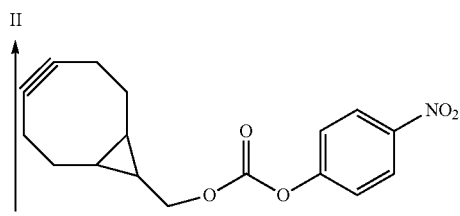

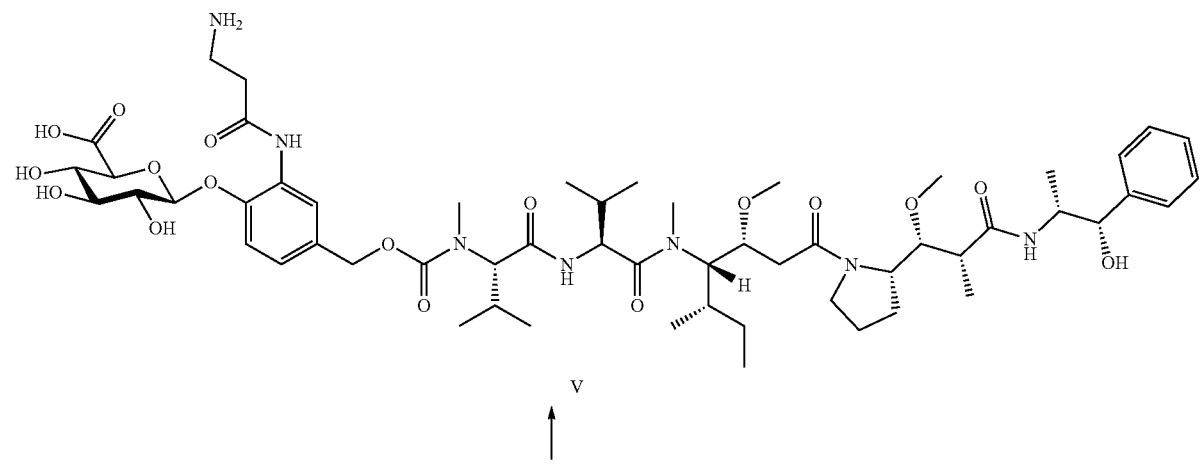

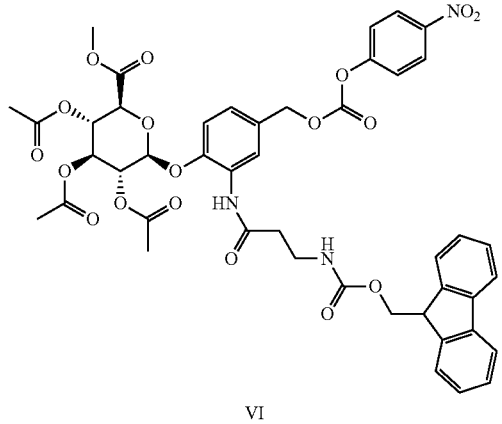

VI

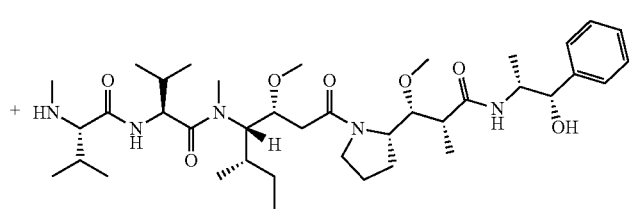

VII

PREPARATIONS AND EXAMPLES

Abbreviations (not exhaustive list)
DAR: Drug to Antibody Ratio
DIPEA: N,N-Diisopropylethylamine
HOBt: Hydroxybenzotriazole
PBS: Phosphate-buffered saline
MMAE: Monomethyl auristatin E
DMF: Dimethylformamide
TFA: Trifluoroacetic acid
DMSO: Dimethyl sulfoxide
MeOH: Methanol
LiOH: Lithium hydroxide
EA: Ethyl Acetate
PE: Petroeum Ether
TCEP: tris(2-carboxyethyl)phosphine
DCM: Dichloromethane
Std. Err: Standard Error
AVG: Average
MFI: mean fluorescence intensity Preparation 1

Synthesis of (2S,3S,4S,5R,6S)-methyl-3,4,5-triacetoxy-6-(4-(hydroxymethyl)-2-nitrophenoxy)-tetrahydro-2H-pyran-2-carboxylate

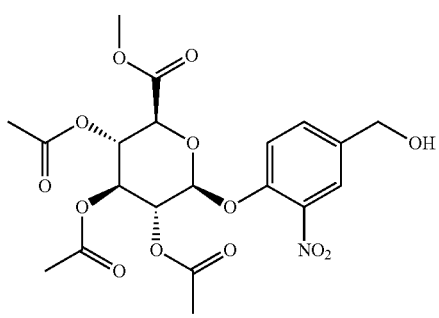 [SMILES: COC(=O)[C@H]1O[C@@H](Oc2ccc(CO)cc2[N+](=O)[O-])[C@H](OC(C)=O)[C@@H](OC(C)=O)[C@@H]1OC(C)=O]

To a solution of (2S,3S,4S,5R,6R)-methyl-3,4,5-triacetoxy-6-bromo-tetrahydro-2H-pyran-2-carboxylate (9.5 g, 23.92 mmoles) in acetonitrile (200 mL) is added 4-(hydroxymethyl)-2-nitrophenol (4 g, 23.65 mmoles). The mixture is cooled to 0° C. while stirring. Silver oxide (27.3 g, 117.81 mmoles) is added slowly to the reaction. The mixture is held at 10° C. with stirring for 20 hr. The material is filtered and washed with ethyl acetate (200 ml). The material is concentrated under vacuum. The crude product is purified by flash chromatography on silica (EA:PE=5:1) to give (2S,3S,4S,5R,6S)-methyl 3,4,5-triacetoxy-6-(4-(hydroxymethyl)-2-nitrophenoxy)-tetrahydro-2H-pyran-2-carboxylate (9.80 g, 85.37% yield) as a yellow solid. MS m/z 508 (M+Na).

Preparation 2

Synthesis of (2S,3S,4S,5R,6S)-methyl 3,4,5-triacetoxy-6-(2-amino-4-(hydroxymethyl) phenoxy)-tetrahydro-2H-pyran-2-carboxylate

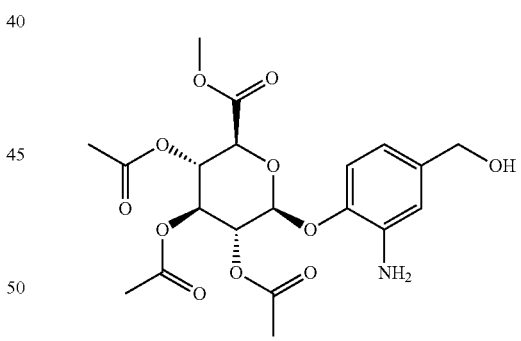

To a solution of (2S,3S,4S,5R,6S)-methyl 3,4,5-triacetoxy-6-(4-(hydroxymethyl)-2-nitrophenoxy)-tetrahydro-2H-pyran-2-carboxylate (9.8 g, 20.19 mmoles) in ethyl acetate (150 mL) is added tetrahydrofuran (150 mL) and platinum dioxide (0.98 g, 4.32 mmoles). The reaction vessel is purged 3 times with hydrogen. The mixture is held at 10° C. with stirring for 20 hr. The material is filtered and washed with ethyl acetate. The material is concentrated under vacuum to give (2S,3S,4S,5R,6S)-methyl 3,4,5-triacetoxy-6-(2-amino-4-(hydroxymethyl)phenoxy)-tetrahydro-2H-pyran-2-carboxylate (8.1 g, 88.09% yield) as a colorless oil. MS m/z 456 (M+H).

Preparation 3

Synthesis of (2S,3S,4S,5R,6S)-methyl-6-(2-(3-(((9H-fluoren-9-yl)methoxy)carbonylamino)-propanamido)-4-(hydroxymethyl)phenoxy)-3,4,5-triacetoxy-tetrahydro-2H-pyran-2-carboxylate

Preparation 4

Synthesis of (2S,3S,4S,5R,6S)-methyl 6-(2-(3-(((9H-fluoren-9-yl)methoxy)carbonylamino)propanamido)-4-(((4-nitrophenoxy)carbonyloxy)methyl)-phenoxy)-3,4,5-triacetoxy-tetrahydro-2H-pyran-2-carboxylate

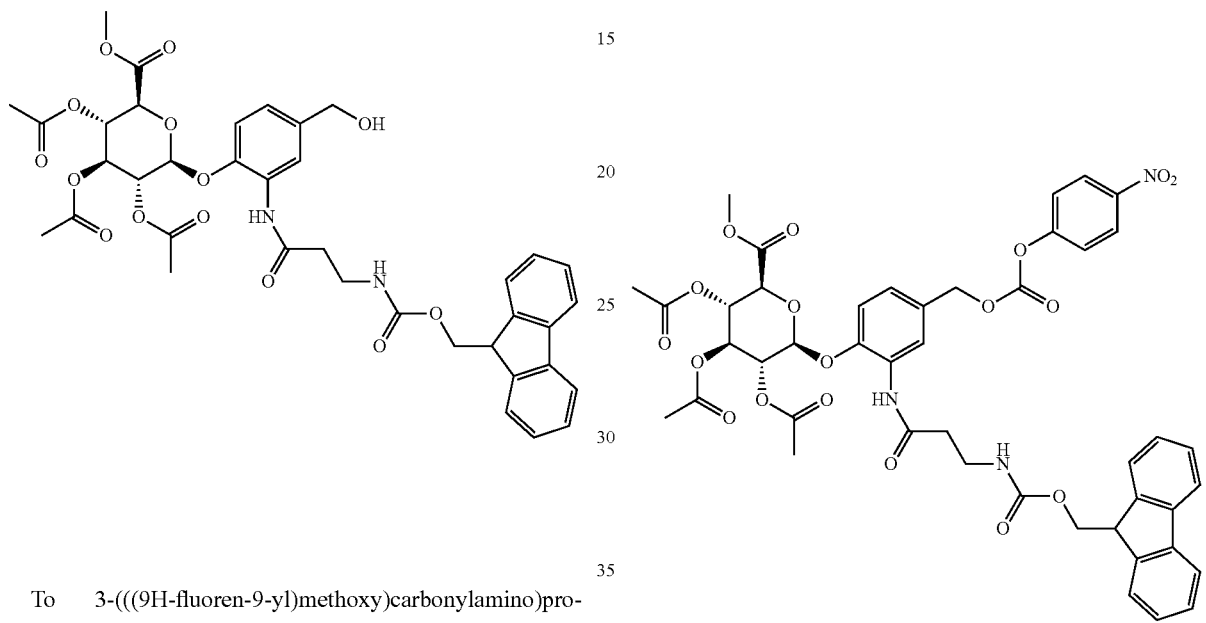

To 3-(((9H-fluoren-9-yl)methoxy)carbonylamino)propanoic acid (5.74 g, 18.44 mmoles) is added tetrahydrofuran (100 mL). The mixture is cooled to 0° C. while stirring. Oxalyl chloride (5 ml, 57.63 mmoles) is added slowly to the reaction. Then three drops of DMF is added to the reaction mixture. The mixture is held at 10° C. with stirring for 2 hours. The material is concentrated under evaporation to provide the corresponding acid chloride. (2S,3S,4S,5R,6S)-Methyl 3,4,5-triacetoxy-6-(2-amino-4-(hydroxymethyl)phenoxy)-tetrahydro-2H-pyran-2-carboxylate (8 g, 17.57 mmoles) is dissolved in dichloromethane (200 mL) and diisopropylethylamine (6 mL, 34.40 mmoles) is added to the vessel with stirring. The mixture is cooled to 0° C. while stirring. The above acid chloride is dissolved in 20 ml DCM and added drop-wise to the reaction mixture. The mixture is held at 10° C. with stirring for 2 hours. The reaction is quenched with aqueous NaHCO$_3$ (50 ml). The mixture is extracted with dichloromethane (100 ml×3) and the aqueous phase is discarded. The material is dried over Na$_2$SO$_4$, filtered, and concentrated to dryness. The crude product is purified by flash chromatography on silica (DCM:EA=1:1) to give (2S,3S,4S,5R,6S)-methyl-6-(2-(3-(((9H-fluoren-9-yl)methoxy)carbonylamino)-propanamido)-4-(hydroxymethyl)phenoxy)-3,4,5-triacetoxy-tetrahydro-2H-pyran-2-carboxylate (7.9 g, 60.06% yield) as yellow oil. MS m/z 749 (M+H).

A mixture of (2S,3S,4S,5R,6S)-methyl 6-(2-(3-(((9H-fluoren-9-yl)methoxy)-carbonylamino)propanamido)-4-(hydroxymethyl)phenoxy)-3,4,5-triacetoxy-tetrahydro-2H-pyran-2-carboxylate (7.2 g, 9.62 mmoles) in dichloromethane (250 mL) and pyridine (3 mL, 37.10 mmoles) is cooled to 0° C. 4-nitrophenyl chloroformate (7.73 g, 38.35 mmoles) in 20 ml DCM is added drop-wise to the reaction mixture. The mixture is held at 0° C. with stirring for 2 hr. The reaction is quenched with aqueous NaHCO$_3$ (150 ml). The mixture is extracted with dichloromethane (150 ml×3) and the aqueous phase is discarded. The material is dried over Na$_2$SO$_4$, filtered, and concentrated to dryness. The crude product is purified by flash chromatography on silica(PE:EA) to give (2S,3S,4S,5R,6S)-methyl 6-(2-(3-(((9H-fluoren-9-yl)methoxy)carbonylamino)propanamido)-4-(((4-nitrophenoxy)carbonyloxy)methyl)-phenoxy)-3,4,5-triacetoxy-tetrahydro-2H-pyran-2-carboxylate (7.02 g, 79.88% yield). MS m/z 914.1 (M+H).

Preparation 5

Synthesis of (3S,4S,6S)-6-[2-(3-aminopropanoylamino)-4-[[[(1S)-1-[[(1S)-1-[[(1S,2R)-4-[(2S)-2-[(1R,2R)-3-[[(1R,2S)-2-hydroxy-1-methyl-2-phenyl-ethyl]amino]-1-methoxy-2-methyl-3-oxo-propyl]pyrrolidin-1-yl]-2-methoxy-1-[(1S)-1-methylpropyl]-4-oxo-butyl]-methyl-carbamoyl]-2-methyl-propyl]carbamoyl]-2-methyl-propyl]-methyl-carbamoyl]oxymethyl]phenoxy]-3,4,5-trihydroxy-tetrahydropyran-2-carboxylic acid (i.e., NH$_2$β-Glucn-MMAE)

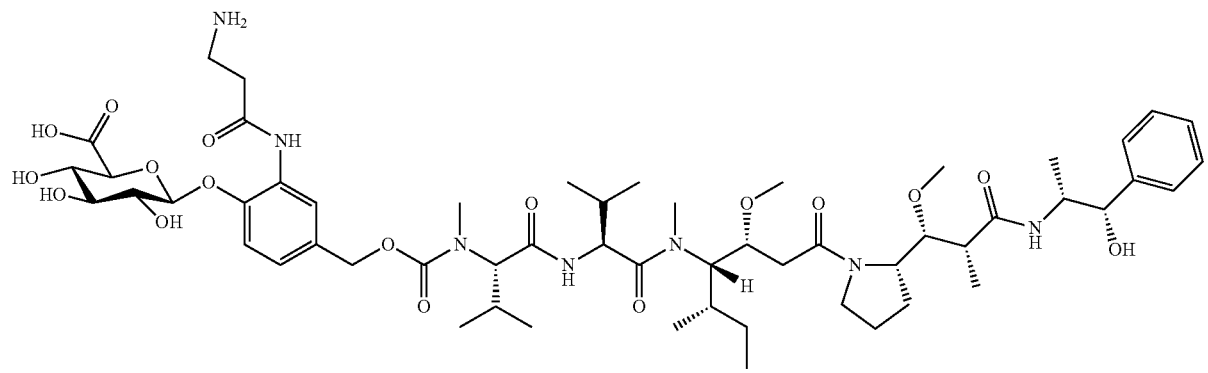

Dissolve methyl (2S,3S,4S,5R,6S)-3,4,5-triacetoxy-6-[2-[3-(9H-fluoren-9-ylmethoxycarbonylamino)propanoylamino]-4-[(4-nitrophenoxy)carbonyloxymethyl]phenoxy]tetrahydropyran-2-carboxylate (155 mg, 0.17 mmol) and (2S)—N-[(1S)-1-[[(1S,2R)-4-[(2S)-2-[(1R,2R)-3-[[(1R,2S)-2-hydroxy-1-methyl-2-phenyl-ethyl]amino]-1-methoxy-2-methyl-3-oxo-propyl]pyrrolidin-1-yl]-2-methoxy-1-[(1S)-1-methylpropyl]-4-oxo-butyl]-methyl-carbamoyl]-2-methyl-propyl]-3-methyl-2-(methylamino)butanamide (MMAE) (146 mg, 0.17 mmol) into DMF (2 mL) and add DIPEA (36 μL, 0.21 mmol) and HOBt (8 mg, 0.059 mmol) to the solution. Stir at room temperature overnight. Add MeOH (1 mL) and 1N LiOH (1 mL). Concentrate and purify by HPLC (Column; Phenomenex Luna 5 μm C18 AXIA packed 30×75 mm column, Mobile phase; A: 0.1% TFA in water, B: 0.1% TFA in Acetonitrile, Monitored; 214 nm, Flow rate; 85 mL/min., Gradient; 10-38%, Gradient time; 8 min.). Dry the collected fractions by lyophilizer to give the desired product, (3S,4S,6S)-6-[2-(3-aminopropanoylamino)-4-[[[(1S)-1-[[(1S)-1-[[(1S,2R)-4-[(2S)-2-[(1R,2R)-3-[[(1R,2S)-2-hydroxy-1-methyl-2-phenyl-ethyl]amino]-1-methoxy-2-methyl-3-oxo-propyl]pyrrolidin-1-yl]-2-methoxy-1-[(1S)-1-methylpropyl]-4-oxo-butyl]-methyl-carbamoyl]-2-methyl-propyl]carbamoyl]-2-methyl-propyl]-methyl-carbamoyl]oxymethyl]phenoxy]-3,4,5-trihydroxy-tetrahydropyran-2-carboxylic acid (NH$_2$-(3-Glucn-MMAE) (122 mg, Yield 64%). MS m/z 1130 (M+H).

Preparation 6

Synthesis of (3S,4S,6S)-6-[2-[3-(9-bicyclo[6.1.0]non-4-ynylmethoxycarbonylamino)propanoylamino]-4-[[[(1S)-1-[ [(1S)-1-[[(1S,2R)-4-[(2S)-2-[(1R,2R)-3-[[(1R,2S)-2-hydroxy-1-methyl-2-phenyl-ethyl]amino]-1-methoxy-2-methyl-3-oxo-propyl]pyrrolidin-1-yl]-2-methoxy-1-[(1S)-1-methylpropyl]-4-oxo-butyl]-methyl-carbamoyl]-2-methyl-propyl]carbamoyl]-2-methyl-propyl]-methyl-carbamoyl]oxymethyl]phenoxy]-3,4,5-trihydroxy-tetrahydropyran-2-carboxylic acid (Octyn-β-Glucn-MMAE)

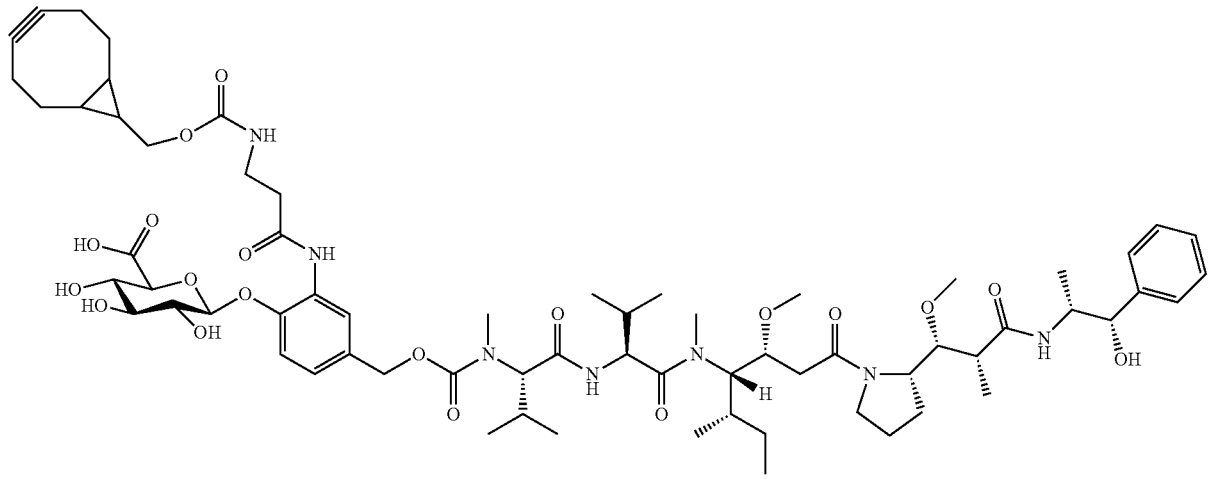

Dissolve (3S,4S,6S)-6-[2-(3-aminopropanoylamino)-4-[[[(1S)-1-[[(1S)-1-[[(1S,2R)-4-[(2S)-2-[(1R,2R)-3-[[(1R,2S)-2-hydroxy-1-methyl-2-phenyl-ethyl]amino]-1-methoxy-2-methyl-3-oxo-propyl]pyrrolidin-1-yl]-2-methoxy-1-[(1S)-1-methylpropyl]-4-oxo-butyl]-methyl-carbamoyl]-2-methyl-propyl]carbamoyl]-2-methyl-propyl]-methyl-carbamoyl]oxymethyl]phenoxy]-3,4,5-trihydroxy-tetrahydropyran-2-carboxylic acid (61 mg, 0.054 mmol) (NH₂β-Glucn-MMAE) to the mixture of DIPEA (19 µL, 0.109 mmol), (1R,9S,9S)-bicyclo[6.1.0]non-4-yl-9-ylmethyl (4-nitrophenyl)carbonate (22 mg, 0.066 mmol) and DMF (0.5 mL). Stir at room temperature overnight. Concentrate and purify by HPLC (Column; Phenomenex Luna 5 uµm C18 AXIA packed 30×75 mm column, Mobile phase; A: 10 mM Ammonium Bicarbonate (pH=10) in water, B: Acetonitrile, Monitored; 214 nm, Flow rate; 85 mL/min., Gradient; 10-46%, Gradient time; 8 min) to give the desired product, (3S,4S,6S)-6-[2-[3-(9-bicyclo[6.1.0]non-4-ynyl-methoxycarbonylamino)propanoylamino]-4-[[[(1S)-1-[[(1S)-1-[[(1S,2R)-4-[(2S)-2-[(1R,2R)-3-[[(1R,2S)-2-hydroxy-1-methyl-2-phenyl-ethyl]amino]-1-methoxy-2-methyl-3-oxo-propyl]pyrrolidin-1-yl]-2-methoxy-1-[(1S)-1-methylpropyl]-4-oxo-butyl]-methyl-carbamoyl]-2-methyl-propyl]carbamoyl]-2-methyl-propyl]-methyl-carbamoyl]oxymethyl]phenoxy]-3,4,5-trihydroxy-tetrahydropyran-2-carboxylic acid (Octyn-β-Glucn-MMAE) (45 mg, Yield 64%) MS m/z 1306 (M+H).

Example 1: Expression and Purification of Anti-MET Antibodies

The anti-MET antibody to be used for generation of the MET ADCs provided herein can be expressed and purified essentially as follows:

A glutamine synthetase (GS) expression vector containing the DNA of SEQ ID NO: 24 (encoding the heavy chain polypeptide having the amino acid sequence of SEQ ID NO: 23) and the DNA of SEQ ID NO: 10 (encoding the light chain polypeptide having the amino acid sequence of SEQ ID NO: 9) is used to transfect the Chinese hamster cell line, CHOK1SV (Lonza Biologics PLC, Slough, United Kingdom) by electroporation. The expression vector encodes an SV Early (Simian Virus 40E) promoter and the gene for GS. Expression of GS allows for the biochemical synthesis of glutamine, an amino acid required by the CHOK1SV cells. Post-transfection, cells undergo bulk selection with 50 µM L-methionine sulfoximine (MSX). The inhibition of GS by MSX is utilized to increase the stringency of selection. Cells with integration of the expression vector cDNA into transcriptionally active regions of the host cell genome are selected against CHOK1SV wild type cells, which express an endogenous level of GS. Transfected pools are plated at low density to allow for close-to-clonal outgrowth of stable expressing cells. The master-wells may be screened for anti-MET IgG expression and then scaled up as needed in serum-free, suspension cultures. Once a suitable cell line is identified, it may be scaled up as needed in serum-free, suspension cultures. Clarified medium, into which the anti-MET IgG has been secreted, is applied to a Protein A affinity column that has been equilibrated with a compatible buffer, such as phosphate buffered saline (pH 7.4) or Tris buffer (pH 7.4). The column is washed to remove nonspecific binding components. The bound anti-MET IgG is eluted, for example, by pH gradient (such as 0.1 M sodium phosphate buffer pH 6.8 to 0.1 M sodium citrate buffer pH 2.5-3.0). Antibody fractions are detected and/or collected, such as by absorbance cutting at 280 nm, SDS-PAGE or analytical size-exclusion. Soluble aggregate and multimers may be effectively removed by common techniques, including size exclusion, hydrophobic interaction, ion exchange, or hydroxyapatite chromatography. The anti-MET IgG may be concentrated and/or sterile filtered using common techniques. The purity of the anti-MET IgG after these chromatography steps is greater than 90%, preferably, greater than 98%. The anti-MET IgG may be immediately frozen at −70° C. or stored at 4° C. for several months.

Example 2: Conjugation of Emibetuzumab

Part A: Conjugation of Emibetuzumab and β-Glucn-MMAE It is understood that the result of the conjugation as described in this Part A of Example 2 is a mixture of MET-ADC #1 conjugates shown below.

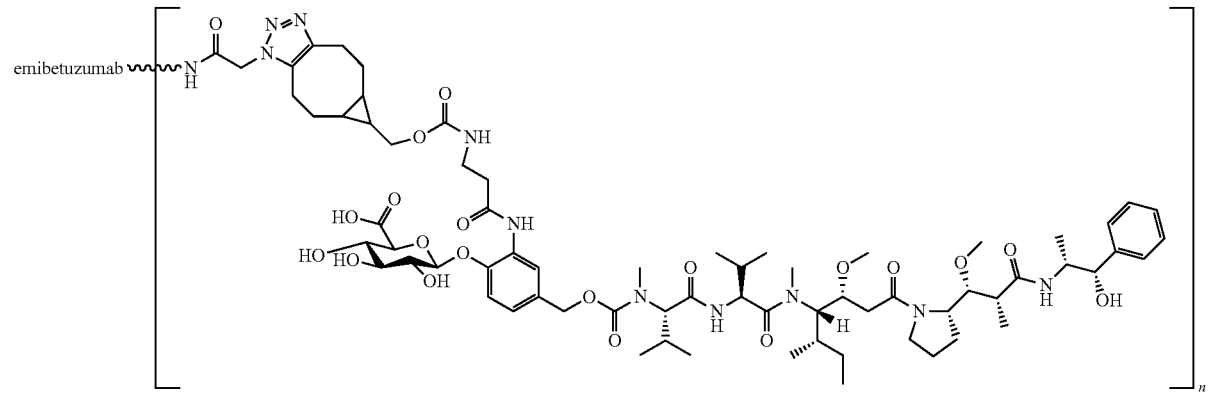

The anti-MET antibody, emibetuzumab, is diluted to a final concentration of 10 mg/mL in PBS buffer, pH 7.0-7.2. A freshly prepared 2 mg/mL solution of (2,5-dioxopyrrolidin-1-yl) 2-azidoacetate solubilized in anhydrous DMSO is added to a final ratio of 7.75-10 molar equivalents of 2,5-dioxopyrrolidin-1-yl 2-azidoacetate to the antibody solution (the exact ratio will depend on the source and purity of 2,5-dioxopyrrolidin-1-yl 2-azidoacetate). The reaction mixture is incubated at 37° C. for 2.5 hours or alternatively at 22° C.±2° C. for >3 hours with gentle mixing. Following the incubation period, the excess unreacted or oxidized 2,5-dioxopyrrolidin-1-yl 2-azidoacetate is removed from the sample using a desalting column, preparative size exclusion chromatography (pSEC), tangential flow filtration (TFF) or dialysis. The concentration of the antibody with 2-azidoacetate is adjusted to 8-10 mg/mL. Octyne-β-Glucn-MMAE (Preparation 6) solubilized in anhydrous DMSO is added to a final ratio of 10-15:1 molar equivalents of Octyne-β-Glucn-MMAE to antibody. The mixture is then incubated at 37° C. for >8 hours or alternatively at 22° C.±2° C. for >16 hours with gentle mixing. Following the incubation, the sample is exchanged into the desired buffer and excess Octyne-β-Glucn-MMAE is removed using a desalting column, preparative size exclusion chromatography (pSEC), tangential flow filtration (TFF), or dialysis.

In order to determine the drug to antibody ratio (DAR), a 50 µl ADC sample at ~1 mg/mL is prepared in PBS. Next, 1.5 µl of 2.5 U/mL N-Glycanase enzyme is added along with 1.5 µl of 5× N-Glycanase reaction buffer, followed by a 4 hour incubation at 37° C. to remove the N-linked glycosylation from the antibodies. Electrospray Ionization Time-of-Flight Mass Spectrometry (ESI-ToF) is used to determine the final average DAR. The sample is passed through an Agilent Poroshell 300SB-C3 column using a 10-80% acetonitrile gradient in 0.1% formic acid, followed by ToF-MS analysis using an Agilent 6230 ToF MS in positive ion mode at a collection rate of 500-10,000 m/z at 1 scan per second.

The DAR of an ADC may be calculated as a product of n and percent of total ion count: DAR contribution=n× percent of total. As an example, for a value of n=2, the DAR contribution is 2×0.203=0.41. The average DAR is a sum of DAR contribution. The highest n detectable may depend on the instrument sensitivity.

As shown in Table 1, the average DAR of the mixture of MET-ADC #1 conjugates prepared essentially as described above in this Example 2 was determined to be approximately 3.3.

TABLE 1

| n | Ion Count | MS m/z | Percent of Total | DAR Contribution |
|---|-----------|--------|------------------|------------------|
| 0 | 190 | 143752 | 2.2 | 0 |
| 1 | 934 | 145138 | 11.0 | 0.11 |
| 2 | 1724 | 146526 | 20.3 | 0.41 |
| 3 | 2079 | 147912 | 24.5 | 0.73 |
| 4 | 1662 | 149339 | 19.6 | 0.78 |
| 5 | 1070 | 150690 | 12.6 | 0.63 |
| 6 | 496 | 152084 | 5.8 | 0.35 |
| 7 | 215 | 153476 | 2.5 | 0.18 |
| 8 | 119 | 154867 | 1.4 | 0.11 |
| | | Average DAR | | 3.3 |

Part B: Conjugation of Emibetuzumab and β-Glucn-MMAE with Alternative Linkers

In methods essentially as described above in Example 2, alternative linkers of various lengths, may be used in place of (2,5-dioxopyrrolidin-1-yl) 2-azidoacetate such as (2,5-dioxopyrrolidin-1-yl) 4-azidobutanoate, azido-PEG4-NHS ester, or azido-PEG8-NHS ester to prepare mixtures of the other MET ADCs specifically referred to herein as MET-ADC #2, MET-ADC #3, or MET-ADC #4, respectively.

Part C: Conjugation of Emibetuzumab and Mal-C-Vc-PABC-MMAE

Using methods well-known in the art, a mixture of MET-ADC #6 conjugates was generated by conjugating emibetuzumb and maleimidocaproyl-valine-citrulline-p-aminobenzoyloxycarbonyl-monomethyl auristatin E (i.e., Mal-C-vc-PABC-MMAE) under conditions optimized to result in a mixture of MET-ADC #6 conjugates having a DAR of approximately 3.3-3.8.

Example 4: Ex Vivo Linker-Payload Conjugate Stability in Mouse Plasma

An important characteristic of an ADC is the stability of the linker between the antibody and the payload (cytotoxic). Rapid release of the payload in blood can be detrimental from both toxicity and potency perspectives. As a means to gain insight into the influence of the composition of the linker on the peripheral blood stability of linker-payload conjugation, ex vivo assessments were conducted using a timed incubation method in murine plasma. Ex vivo plasma linker-payload conjugate stability in murine matrix was employed to assess the degree of conjugate stability conferred by the linkers within MET-ADC #2, MET-ADC #3 and MET-ADC #4. The linker-payload stability profiles for MET-ADC #2, MET-ADC #3 and MET-ADC-#4 were characterized by measuring the DAR (drug to antibody ratio) after each ADC was spiked mouse plasma for 72 hours at 37° C. The DAR following the plasma incubation was compared to the initial DAR prior to incubation (Table 2). The DAR for each ADC was determined using a bead-based anti-human IgG immuno-affinity capture method. Following capture of the ADC, the samples were deglycosylated (on the bead), eluted using acid and reduced prior to detection of heavy and light chain structures using a LC-MS system (Q-TOF) as reported (see, for example, Kaur, S., et al., Bioanalytical assay strategies for the development of antibody-drug conjugate biotherapeutics. Bioanalysis, 2013, 5(2):201-226). The ex vivo murine plasma findings show the rank order of conjugate stability conferred by the linkers is MET-ADC #2>MET-ADC #3>MET-ADC #4. The data indicate the shorter linkers with increased hydrophobic content conferred increased conjugate stability with the MET antibody, emibetuzumab.

TABLE 2

| MET ADC molecule | Initial DAR | % Of The Initial DAR Remaining Following Incubation In Mouse Plasma (72 hr./37° C.) |
|---|---|---|
| MET-ADC#2 | 4.7 | 112.5 |
| MET-ADC#3 | 3.6 | 42.2 |
| MET-ADC#4 | 3.7 | 12.9 |

Example 5: Pharmacokinetics and Linker-Payload Conjugate Stability in Mice

The total IgG and conjugated IgG payload pharmacokinetics of MET-ADC #1 and MET-ADC #2 were characterized in male CD-1 mice after a single intravenous (IV) dose at a single dose level of 2.5 mg/kg to assess their exposure profiles and linker-payload stability in an in vivo system. The total IgG concentrations and conjugated IgG payload were determined using a bead-based anti-human IgG immuno-affinity capture method. Following capture of the ADC, the total IgG samples were reduced, alkylated and treated with trypsin prior to detection of the heavy chains using LC-MS. For IgG conjugated payload analyses, samples were additionally treated with β-glucuronidase which leads to hydrolysis of the glycosidic linkage and liberates (i.e., deconjugates) payload (MMAE) from the antibody. The payload liberated is quantitated by LC-MS/MS to determine the conjugated IgG payload concentrations.

The mouse PK parameters are presented in Table 3. The murine PK parameters (Cmax, AUC, CL and T1/2) derived from the total IgG compared to the conjugated IgG payload analyses of MET-ADC #1 are reasonably similar (Table 3). The total IgG and conjugated IgG payload derived clearance (CL) values for MET-ADC #1 are 0.4 mL/hr/kg while the elimination half-life ($T_{1/2}$) values are ~187 hours and ~125 hours, respectively. The comparable CL values derived from the two analyses indicate the linker-payload component of MET-ADC #1 is stable in the murine blood circulation.

The total IgG and conjugated IgG payload derived clearance (CL) values for MET-ADC #2 show an ~2-fold difference (Table 3) with values of 0.3 and 0.6 mL/hr/kg, respectively. The elimination half-life ($T_{1/2}$) values for MET-ADC #2 are 175 and 80 hours in the total IgG and conjugated IgG payload assays, respectively. The larger difference in the total IgG and conjugated IgG payload CL values observed for MET-ADC #2 suggest the molecule may not be as stable in vivo as MET-ADC #1.

TABLE 3

| Dose (mg/kg)/ Route/ ADC# | Assay Format | $C_{max}^a$ (μg/mL) | $AUC_{0-last}^b$ (μg*hr/mL) | $AUC_{0-\infty}^b$ (μg*hr/mL) | $Vss^c$ (mL/kg) | $t_{1/2}^d$ (hr) | $CL^e$ (mL/hr/kg) |
|---|---|---|---|---|---|---|---|
| 2.5/IV/ ADC#1 | Total IgG | 56.0 | 5035 | 6915 | 94 | 187 | 0.4 |
|  | IgG CP* | 38.1 | 4778 | 5714 | 87 | 125 | 0.4 |
| 2.5/IV/ ADC#2 | Total IgG | 78.3 | 6206 | 9283 | 80 | 175 | 0.3 |
|  | IgG CP* | 45.8 | 3816 | 4199 | 93 | 80 | 0.6 |

*IgG CP = Conjugated IgG payload
$^a$Mean maximum observed serum concentration.
$^b$Area under the serum concentration-time curve measured from 0 to last hour or to infinity.
$^c$Volume of distribution at steady state.
$^d$Elimination half-life.
$^e$Total body clearance.

Example 6: Binding Analysis of Emibetuzumab and MET-ADC #1 to MET-ECD

A surface plasmon resonance biosensor such as a BIAcore® 2000, BIAcore® 3000, or a BIAcore® T100 (Biacore Life Sciences Division, GE Healthcare, Piscataway, N.J.) may be used to measure binding kinetics and affinity of antibodies and ADCs according to methods known in the art. Except as noted, all reagents and materials can be purchased from BIAcore® AB (Upsala, Sweden), and measurements may be performed at 37° C. to mimic physiological conditions.

Briefly described, samples may be dissolved in HBS-EP buffer (150 mM sodium chloride, 3 mM EDTA, 0.005% (w/v) surfactant P-20, and 10 mM N-2-hydroxyethyl-piperazine-N'-2-ethanesulfonic acid (HEPES) at pH 7.4 or 7.6). A CM5 S sensor chip containing immobilized protein A (which may be generated using standard NHS-EDC amine coupling) on all four flow cells (Fc) may be used to employ a capture methodology. Antibody or ADC samples can be prepared at 0.5 μg/mL by dilution into running buffer initially and then their capture may be tested at flow rate 10 μl/min for 1 minute. Based on the amount captured, the antibody or ADC concentration or injection time can be adjusted accordingly to target the desired capture amount between about 25 RU to 35 RU. MET-ECD may be prepared at final concentrations of 100, 50, 25, 12.5, 6.25, 3.13, 1.56, 0.78, 0.39, 0.2 and 0 (blank) nM by dilution into running buffer. Each analysis cycle may consist of: (1) capturing antibody samples on separate flow cells (Fc2, Fc3, and Fc4); (2) injection of 250 μL (150-sec) of MET-ECD over all Fc at 100 μL/min; (3) return to buffer flow for 20 minutes to monitor dissociation phase and (4) regeneration of chip surfaces with a 5 μL (30-sec) injection of glycine, pH 1.5 over all Fc at 10 μL/min. Data can be processed using standard double-referencing and fit to a 1:1 binding model using Biacore T100 Evaluation software, version 2.0 or Biacore T200 Evaluation software, version 1.0, to determine the association rate ($k_{on}$, $M^{-1}s^{-1}$ units), dissociation rate ($k_{off}$, $s^{-1}$ units), $R_{max}$ (RU units), and binding affinity KD (nM).

The equilibrium dissociation constant ($K_D$) is calculated as from the relationship $K_D=k_{off}/k_{on}$.

MET-ADC #1 was tested as described above to determine its binding kinetics and binding affinity to MET-ECD. The results are summarized in Table 4 below. MET-ADC #1 binds MET-ECD with binding affinity ($K_D$) comparable to that of emibetuzumab.

TABLE 4

Binding Kinetics and Affinity of MET ADC and Emibetuzumab to MET-ECD

| Antibody or ADC | $k_{on}$ $M^{-1}s^{-1}$ ($10^4$) | $k_{off}$ $s^{-1}$ ($10^{-5}$) | $K_D$ (nM) |
|---|---|---|---|
| Emibetuzumab | 6.86 ± 1.18 × $10^4$ | 5.46 ± 0.52 × $10^4$ | 7.93 ± 1.02 |
| MET-ADC#1 | 7.88 ± 1.14 × $10^4$ | 4.84 ± 0.14 × $10^4$ | 6.24 ± 0.96 |

Determined from 3 independent experiments at 37° C. (± Std Dev)

Example 7: MET-ADC #1 does not have Increased Agonist Activity as Compared to Emibutuzumab The difficulty of generating high-binding affinity MET antibodies without significant agonist activity has been well-documented in the art. For example, Sato, et al., reported that "the discovery of therapeutic antibodies against MET has been very difficult, and antibodies that compete with HGF typically act as agonists by dimerizing the receptor (Sato, et al., *Neoplasia,* 11:4 pp. 355-364, (2009) citing Prat, M., et al., *J Cell Sci* 111 (Pt 2), 237-247 (1998)). Additionally, both WO 1996/38557 and WO 2010/059654 describe various MET antibodies (including 5D5 and OptD11, respectively) that are shown to have agonist activity. Therefore, some MET antibodies developed for clinical settings (e.g., 5D5) were engineered to be monovalent (i.e., one-armed) in an attempt to reduce the agonistic activity of such cMET antibodies to acceptable levels for clinical study of anti-cancer activity if the antibody was modified into a monovalent (i.e., one-armed) antibody (Jin, H., et al., MetMab, the one-armed 5D5 anti-c-Met antibody, inhibits orthotopic pancreatic tumor growth and improves survival. *Cancer Res* 68, 4360-4368 (2008)). However, reducing the valency of the compound with respect to its binding of MET (monovalent as compared to bivalent) can be expected to reduce its anti-tumor activity in vivo. Liu, L., et al., Clin Cancer Res; 20(23); 6059-70 (2014) previously reported that a battery of in vitro bioassays was used to characterize the agonist properties of various MET antibodies (including C8-H241-IgG4) using HGF and agonist bivalent MET antibody 5D5 as positive controls. Liu, et al., (2014) previously reported that emibetuzumab induced only a weak and transient phosphorylation of pan-AKT upon binding to MET, and this weak phosphorylation of pan-AKT did not stimulate biologic activity in seven (7) functional MET agonist assays. However, the higher levels of AKT phosphorylation induced by MET antibody 5D5 and OptD11 correlated well with cell proliferation, mobility, and anti-apoptosis (i.e., activities which are undesirable for intended use as a cancer therapeutic agent) in the same functional assays (Liu, et al., (2014)).

Because it has been reported that MET agonistic antibodies increased hepatocyte proliferation and toxicity, a phosphor-AKT assay may be used to test MET-ADCs for MET agonist activity. Briefly stated, Caki-1 cells may be starved overnight in serum-free medium with 0.1% BSA and then treated with ADCs or naked MET antibodies at 5 µg/mL for the desired durations. Cell lysates may be analyzed for phosphorylation of pan-AKT by MSD ELISA, for example.

Figure 2:
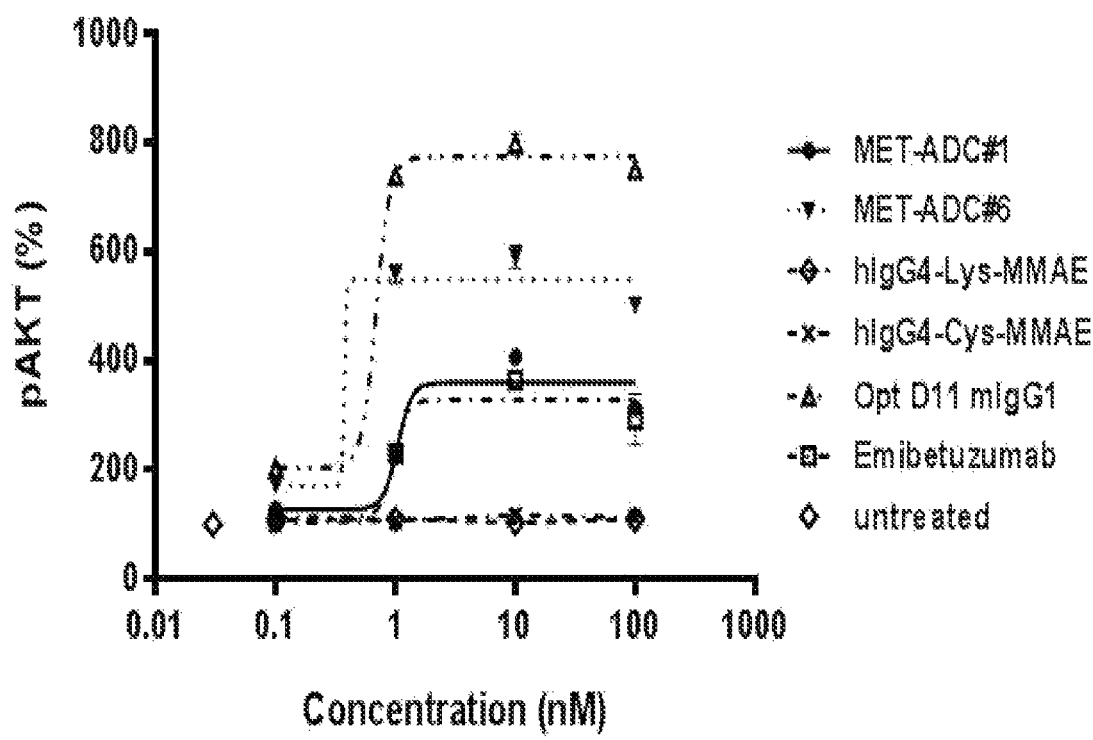
FIG. 2 shows results of an in vitro bioassay measuring induction of pan-AKT phosphorylation (pAKT) in Caki-1 cells indicating that MET-ADC #1 does not have increased agonist activity as compared with emibetuzumab.

In an in vitro phosphor-AKT bioassay performed essentially as described above in this Example 7, MET-ADC #1 was determined to have the same low to no agonist activity as its unconjugated parental antibody, emibetuzumab (see FIG. 2). In the same assay, agonistic bivalent MET antibody optD11 was used as positive control (see FIG. 2). Surprisingly, other conjugation methods employed with emibetuzumab (for instance, MET-ADC #6 (see FIG. 2)) resulted in a MET-ADC conjugate having significant increased agonist activity as compared to MET-ADC #1 and/or unconjugated emibetuzumab.

Example 8: Binding of MET-ADC #1 to Cell Surface MET on Colon Cancer Cell Line HT-29 is Comparable to Unconjugated Parental MET Ab, Emibetuzumab The colon cancer cell line HT-29 (ATCC, Manassas, Va.; catalog # HTB38D) expresses high levels of MET on the surface and harbors at least BRAF, P53 and PIK3 mutations. To determine whether the binding affinity to cell surface MET was maintained in MET-ADC #1 as compared to unconjugated parental antibody, HT-29 colon cancer cells may be suspended in FACS buffer containing Alexa 488 labelled emibetuzumab and 2-fold dilutions of 100 nM of the unlabeled emibetuzumab or MET-ADC #1 for 45 minutes on ice. The cells may be washed twice with the buffer and FACS analysis may be used to measure the abilities of MET-ADCs or MET antibodies to compete with Alexa 488-labelled emibetuzumab for binding to MET on surface of HT-29 tumor cells.

Experiments to determine binding of MET-ADCs and MET antibodies to MET protein expressed on the cell surface were performed essentially as described above in Example 8. As shown in FIG. 1, MET-ADC #1 was shown to exhibit binding activity to HT-29 expressed cell surface MET that is comparable to unconjugated, parental MET antibody, emibetuzumab (FIG. 1).

Figure 3:
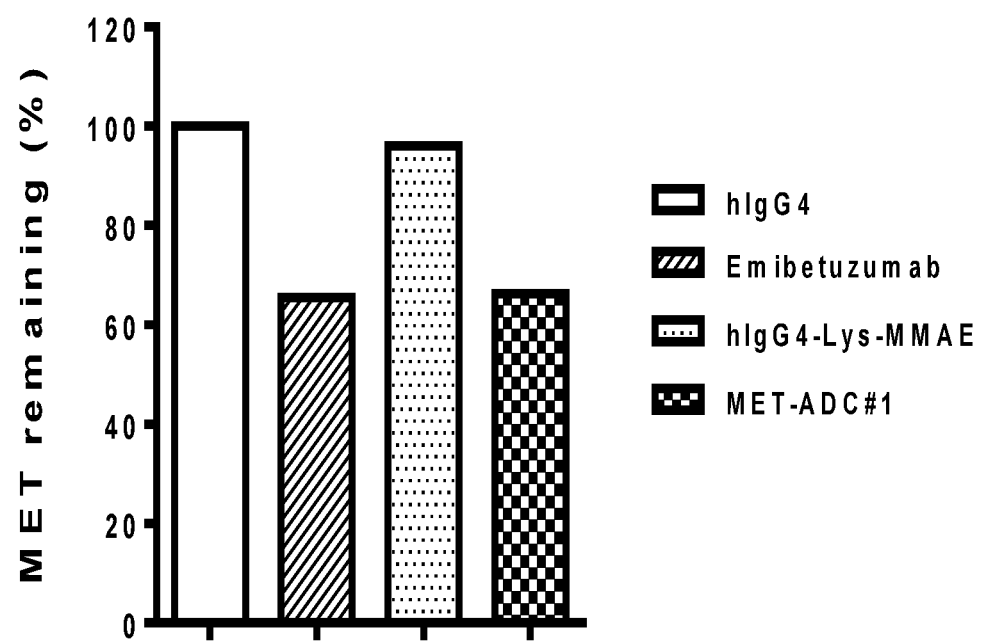
FIG. 3 shows that MET-ADC #1 exhibits internalization activity similar to that of emibetuzumab in pancreatic tumor BXP3 cells as determined by FACS analysis of cell surface MET changes in the cells after treatment with MET-ADC #1, emibetuzumab, isotype control ADC (i.e., hIgG4 Lys-MMAE), or isotype control (i.e., hIgG4).
Figure 4:
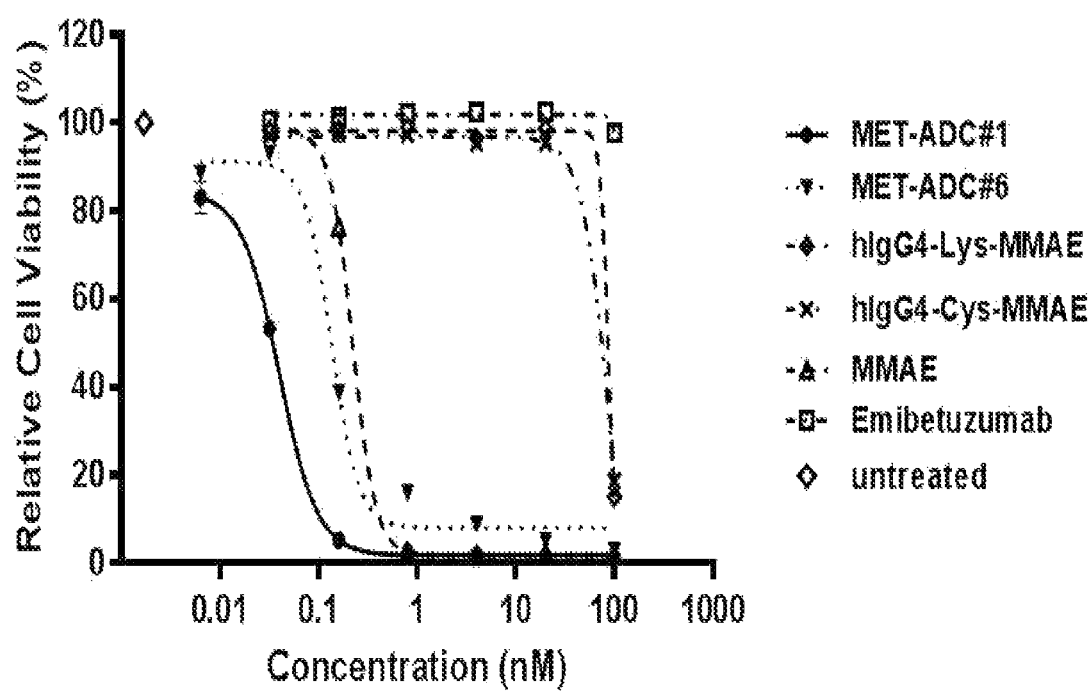
FIG. 4 shows the activity of MET-ADC #1 in an in vitro HT-29 cell-killing assay. MET-ADC #1 is highly potent in killing HT-29 cells in this assay.
Figure 5:
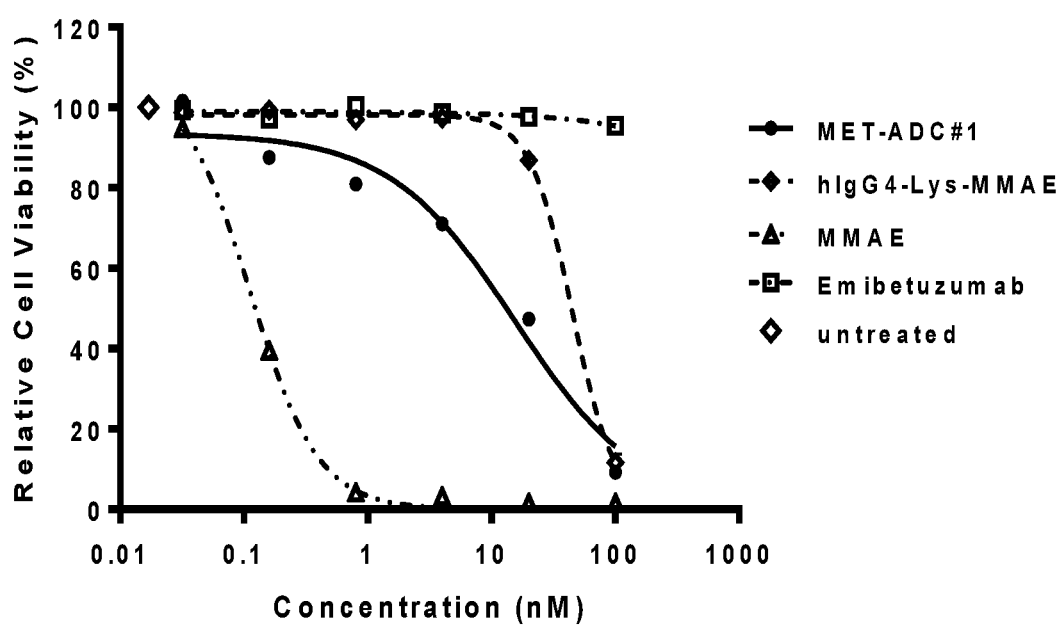
FIG. 5 shows the activity of MET-ADC #1 in an in vitro RKO cell-killing assay. MET-ADC #1 is highly potent in killing RKO cells in this assay.

Example 9: MET-ADC #1 and Emibetuzumab Exhibits Comparable Activity for Internalization of Cell Surface MET To measure whether MET-ADC #1 induces MET internalization similarly to it's parental MET antibody emibituzumab, cells were treated overnight with a final concentration of 33 nmol/L of MET-ADC #1, emibetuzumab, control IgG4-Lys-MMAE, or control IgG4 and dissociated with enzyme-free dissociation solution. Dissociated cells were labeled for 1 hour with 2 mg/mL of a Alexa Fluor 488-labeled Lilly proprietary MET detection antibody (which binds a separate epitope than emibetuzumab). 10,000 events were acquired by FACS for each sample. The results were plotted as the percentage of emibetuzumab or MET-ADC #1 treated samples over the control IgG4 or control IgG4-Lys-MMAE. MET-ADC #1 showed comparable internalization rate as emibetuzumab (FIG. 3).

Example 10: MET-ADC #1 Kills MET Overexpressing Tumor Cells Regardless of Various Known Resistance Conferring Mutations The colon cancer cell line HT-29 has been shown to express high levels of MET (approximately 161,000 MET receptors/cell) as well as harboring BRAF mutation(s). Therefore, the HT-29 cell line may be used to determine if test MET-ADCs can kill MET overexpressing tumor cells in vitro.

Briefly described, 2-3×10³ cells/well in 100 µL of culture medium may be plated in 96 well plates and incubated overnight at 37° C., 5% $CO_2$. The MET-ADCs, MET antibody(ies), control MMAE or control hIgG4 conjugated to MMAE with cysteine conjugation antibody(ies) may be diluted 1:3 in serum-free culture medium starting from 100 nM (final) in 50 µL as 3× concentrations to the HT-29 cells. At the end of an additional 5-6 days of cell growth at 37° C. in a humidified incubator with 5% $CO_2$, the plates may be equilibrated to room temperature for 30 minutes and 100 µL/well of CellTiter-Glo® reagent (Promega Corp., Fitchburg, Wis.) may then be added to assess cell viability. Cell viability may be determined by measuring luminescence.

Assays performed essentially as described in this Example 10 demonstrate that MET-ADC #1 kills MET expressing HT-29 tumor cells better than the parental anti-MET antibody, emibetuzumab, free MMAE, or a combination of emibetuzumab and free MMAE. More specifically, MET-ADC #1 killed HT-29 cells with $EC_{50}$=0.038+/−0.007 nM and higher and a non-binding control hIgG4 lysine conjugated to MMAE (i.e., hIgG4-Lys-MMAE) was also included in all assays to confirm that cell killing was antigen dependent. Surprisingly, MET-ADC #6 is less active than MET-ADC #1, indicating that the optimizing link, payload and conjugation methods with the same antibody make difference on anti-tumor activity. The parental antibody, emibetuzumab, and hIgG4-MMAE control showed no significant cell killing activity in HT-29 cells. Interestingly, ABBV-399, a MET-ADC comprising the anti-MET antibody, ABT-700, conjugated through cysteine residues with MMAE demonstrated an $EC_{50}$=9.0+/−1.4 nM in a HT-29 killing assay (Strickler, J. H., et al.) conducted essentially as described in this part A of Example 10. The 200-fold greater potency in killing HT-29 tumors cells observed with MET-ADC #1 as compared to ABBV-399 is just one example of the surprising functional differences between MET-ADC #1 from ABBV-399.

In similar experiments using other cells, MET-ADC #1 killed RKO (BRAF, PIK3), CXF-269L (TP53) and LS411N (BRAF, PIK3) colon cancer cells overexpressing MET in spite of downstream mutations indicated (data not shown) and varying levels of MET expression (i.e., MET density of approximately 16,000-50,000, 185,000, and 198,000 receptors/cell, respectively). In addition, MET-ADC #1 showed superior killing activity than MET-ADC #6 (i.e., emibetuzumab-Mal-vc-PABC-MMAE).

Example 11: Correlation of Tumor Cell MET Expression Level and Sensitivity to MET-ADC Various tumor cell lines and normal human cells may be tested for MET-ADC induced cell killing activity essentially as described above in Example 10 as assessed for MET receptor density. MET cell surface density was determined by indirect immunofluorescence staining of cell surface antigens on cultured cells using QIFIKIT (Dako). Briefly, cells may be harvested from a culture flask as described above for FACS analysis, added to 96-well plates and incubated at 4° C. with 5 µg/mL emibetuzumab or hIgG4. Following a forty-five minute incubation, cells may be incubated for 1 hour on ice with FITC conjugated antibody diluted 1:50 in FACS buffer. Then cells may be washed and receptor numbers may be determined by indirect immunofluorescence staining of the QIFIKIT beads using a Becton Dickinson LSRII flow cytometer.

The results of experiments performed essentially as described in Examples 10 and 11 are summarized in the Table 10. Briefly stated, MET-ADC #1 killed RKO tumor cells having as low as 16,000 receptors/cells, but was less effective at killing normal human endothelial cells with similar receptor numbers. Overall, MET receptor numbers correlate with killing activity except the autocrine HGF-KP4, which showed enhanced killing at lower receptor density and CFPAC-1 becoming resistant due to poor internalization. In stark contrast of the results observed with MET-ADC #1, ABBV-399 mediated tumor cell killing has been reported to have an approximate threshold of MET cell surface molecules >100,000 for sensitivity to ABBV-399, a MET ADC comprising the MET antibody, ABT-700, conjugated through cysteine residues with monomethyl auristatin E (see, Strickler, J. H., et al., Phase 1, open-label, dose-escalation and expansion study of ABBV-399, an antibody drug conjugate (ADC) targeting c-Met, in patients (pts) with advanced solid tumors, J. Clin. Oncol. 34, (suppl; abstr 2510) (2016)). Furthermore, MET-ADC #1 demonstrated cell killing activities in various MET overexpressing tumors including gastric, colorectal, pancreatic, ovarian cancers; liver carcinoma, glioblastoma; lung, prostate and head and neck cancers (Table 10). MET-ADC #1 may kill tumor cells with an approximate threshold of MET cell surface density >32,000 receptor per cells if the tumor cells are sensitive to MMAE, not secreting HGF.

TABLE 10

| Run | Cell Types | Cell lines | Cell surface MET numbers (x10e3) | MET-ADC#1 Max Killing % | MET-ADC#1 EC50 (nM) +/− SD | Sensitive/ Resistant |
|---|---|---|---|---|---|---|
| N = 3 | PANC Ca | Aspc-1 | 54 | 81 | 0.028 +/− 0.01 | S |
|  | PANC Ca | Capan-2 | 63 | 58 | 0.26 +/− 0.22 | PS |
|  | PANC Ca | #KP-4 | 15 | 91 | 0.1809 +/− 0.017 | S |
|  | PANC Ca | Hs 766T | 67 | 57 | 0.37 +/− 0.22 | PS |
|  | PANC Ca | BxPC-3 | 33 | 96 | 0.07 +/− 0.03 | S |
|  | PANC Ca | CFPAC-1 | 65 | 35 | >100 | R |
|  | PANC Ca | HPAF-II | 24 | 84 | 0.10 +/− 0.07 | S |
|  | PANC Ca | Capan-1 | 51 | 69 | 0.72 +/− 1.26 | PS |
|  | PANC Ca | Panc-1 | 7 | 55 | >100 | R |
|  | PANC Ca | Su.86.86 | 5 | 33 | >100 | R |
|  | PANC Ca | SW 1990 | 7 | 52 | >100 | R |
|  | PANC Ca | MiaPaca-2 | not detectable | 35 | >100 | R |
| N = 4 | Colorectal Ca | #HT29 | 161 | 98 | 0.038 +/− 0.007 | S |
| N = 2 | Colorectal Ca | **RKO | 16 | 87 | 24.03 +/− 8.5 | PS |

TABLE 10-continued

| Run | Cell Types | Cell lines | Cell surface MET numbers (x10e3) | MET-ADC#1 Max Killing % | MET-ADC#1 EC50 (nM) +/− SD | Sensitive/ Resistant |
|---|---|---|---|---|---|---|
| N = 1 | Colorectal Ca | **LoVo | 70 | 64 | 6.68 | PS |
| | Colorectal Ca | **LS411N | 181 | 84 | 0.05 | S |
| | Colorectal Ca | **HCT-116 | 133 | 46 | >100 | R |
| | Colorectal Ca | **CXF-269L | 186 | 66 | 0.11 | S |
| | Colorectal Ca | **GEO | 63 | 46 | >100 | R |
| | Colorectal Ca | **CXF-1103L | 49 | 95 | 26.71 | PS |
| | Colorectal Ca | **Caco-2 | 55 | 22 | >100 | R |
| N = 3 | NSCLC | #EBC-1 | 233 | 97 | 0.06 +/− 0.005 | S |
| | Gastric Ca | #SNU-5 | 291 | 99 | 0.15 +/− 0.001 | S |
| | Gastric Ca | #Hs 746T | 350 | 79 | 0.12 +/− 0.03 | S |
| | Glioblastoma | #U-87MG | 22 | 89 | 8.68 +/− 1.5 | PS |
| | NSCLC | H1993 | 391 | 93 | 0.073 +/− 0.013 | S |
| | NSCLC | #A549 | 43 | 59 | 45.45 +/− 8.67 | PS |
| | NSCLC | #H441 | 197 | 75 | 0.052 +/− 0.058 | S |
| N = 2 | NSCLC | HCC827 | 111 | 71 | 0.089 +/− 0.057 | S |
| | Cholangiocarcinoma | *SNU869 | 58 | 82 | 0.052 +/− 0.026 | S |
| | Cholangiocarcinoma | *SNU1196 | 23 | 43 | >100 | R |
| | Liver Ca | *EGI-1 | 76 | 66 | 36.84 +/− 18.2 | PS |
| | head and neck cancer | *Cal27 | 44 | 96 | 7.34 +/− 6.35 | S |
| | Cholangiocarcinoma | *Sun245 | 29 | −19 | >100 | VR |
| | Breast Ca | *T47D | not detectable | 27 | >100 | R |
| N = 1 | NSCLC | NCI-H292 | 78 | 81 | 5.863 | S |
| | NSCLC | L55 | N/A | 40 | >100 | R |
| | Ovarian Ca | OV79 | 64 | 84 | 1.565 | S |
| | Prostatic Ca | PC3 | 32 | 82 | 0.0279 | S |
| | Rhabdomyosarcoma | A204 | not detectable | 15 | >100 | R |
| | | Non-tumor human cell lines | | | | |
| N = 1 | aortic endothelia cell | HuAEC | 13 | 71 | 57.61 nM | R |
| | aortic smooth muscule cell | AOSMC | 3 | 64 | >100 nM | R |
| | renal proximal tubul cell | RPTEC | 79 | 40 | >100 nM | R |
| | humen fresh hepatocyte | Hepatocyte | N/A | | >100 nM | R |
| 3 donors | humen fresh naïve PBMC | PBMC | N/A | | >100 nM | R |
| | humen fresh activated PBMC | PBMC | N/A | | >100 nM | R |

MET number expression according to published data
**MET number expression using Quantum beads, other unmarkers using Qifikit beads
*MET expression (Mean Flurorescence Intensity): with AF488-emibetuzumab staining

Example 12: Inhibition of Tumor Growth in Mouse Xenograft Models for CRC (HT-29), Pancreatic (Bxpc3 and KP-4), Gastric (Hs746t), and Lung (Calu-6) Cancer Female athymic nude mice age 6- to 7-weeks old are available commercially, including from Harlan Laboratories (Indianapolis, Ind.). The mice are allowed to acclimate for one week and fed ad libitum on a normal low fat (4.5%) diet, which may be continued for the duration of the study. Tumor cells may be purchased from ATCC and may be cultured in cell culture media such as RPMI 1640 (Life Technologies) with L-glutamine, 25 mM HEPES supplemented with 10% FBS and 1 mM Na Pyruvate. Cells may be detached, washed with serum free medium and then resuspended at a final concentration of $50 \times 10^6$ cells/mL in serum free RPMI 1640. Tumor cells, approximately $5 \times 10^6$, may be injected subcutaneously in the rear flank of subject mice in a 1:1 mixture of serum free growth medium and Matrigel (Becton Dickinson, Bedford, Mass.). Tumor and body weight measurements may be performed twice weekly. Prior to treatment, mice can be randomized based on tumor size using a randomization algorithm. Treatments may be started when the average tumor volume reaches 100 mm³. The randomized mice were separated into different groups and dosed with antibodies through tail vein injection once a week.

MET-ADCs and control hIgG4-MMAE may be prepared in Phosphate Buffered Saline (PBS) prior to dose. Tumor size may be determined by caliper measurements. Tumor volume (mm³) may be estimated from the formula $A^2 \times B \times 0.536$, where A is the smaller and B is the larger of perpendicular diameters. Tumor volume data can be transformed to a log scale to equalize variance across time and treatment groups. Log volume data can be analyzed with two-way repeated measures ANOVA by time and treatment using SAS PROC MIXED software (SAS Institutes Inc, Cary, N.C.). Treatment groups are compared with the specified control group at each time point.

Figure 6:
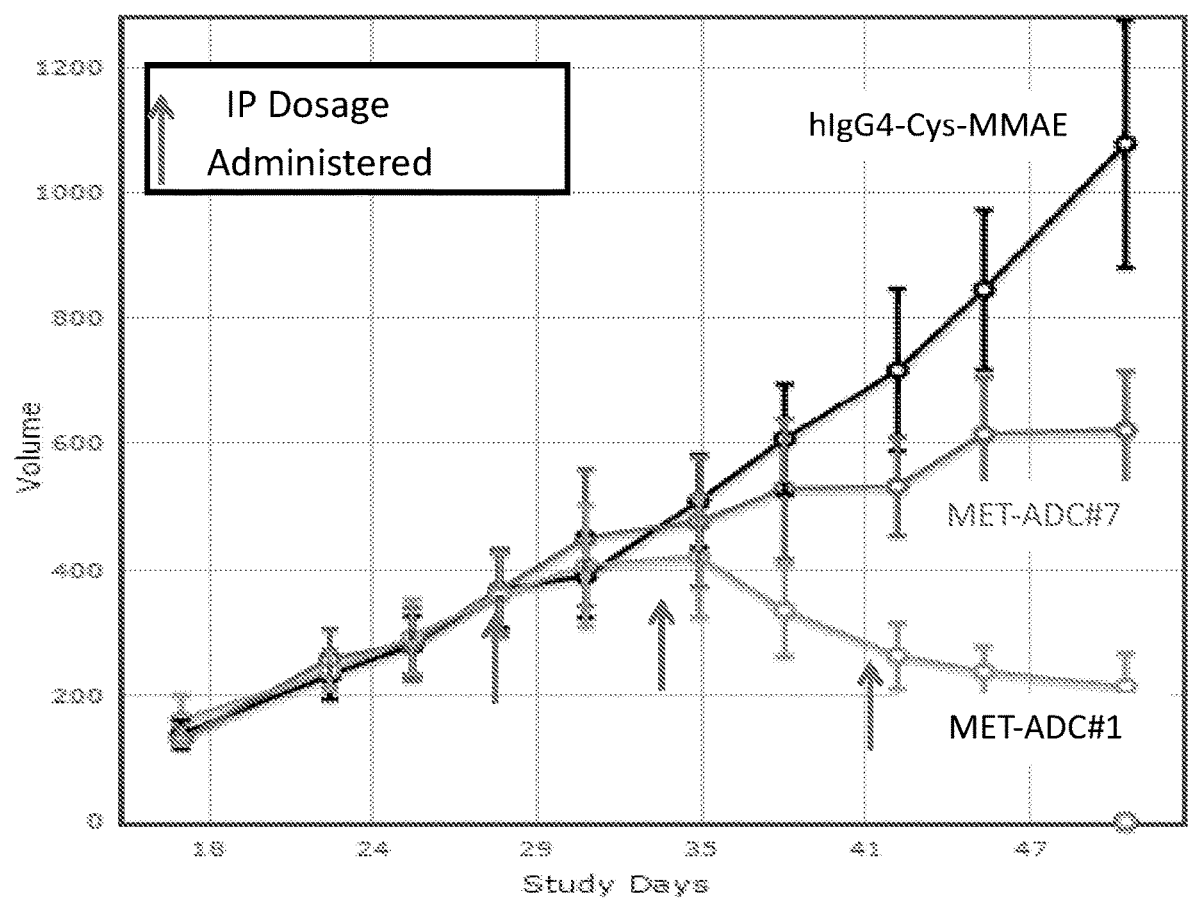
FIG. 6 shows the efficacy of MET-ADC #1 and MET-ADC #7 (i.e., C8-H241-IgG2-Cys-MMAE) in an in vivo HT-29 xenograft model.

Part A:

Immunodeficient mice bearing HT-29 colon cancer tumor xenografts were generated as described above in this Example 12 and treated once a week for 3 consecutive weeks with MET-ADC #1 and MET-ADC #7. The results are summarized in Table 11. FIG. 6 illustrates the treatment results of MET-ADC #1, MET-ADC #7 (i.e., C8-H241-IgG2-Cys-MMAE), and hIgG4-Cys-MMAE control at 1 mg/kg, 1 mg/kg, and 3 mg/kg, respectively.

When tested in HT-29 xenografts, MET-ADC #1 showed far superior efficacy when compared to the hIgG4-Cys-MMAE or MET-ADC #7 (see FIG. 6). In separate experiment(s) conducted essentially as described in the Example 12, the unconjugated, parental antibody, emibetuzumab, did not inhibit HT-29 tumor growth (data not shown).

TABLE 11

Summary of MET-ADC efficacy in HT-29 mouse xenograft models*

| MET-ADC | Observation |
| --- | --- |
| MET-ADC#1 | Tumor regression^ |
| MET-ADC#2 | Tumor regression* |
| MET-ADC#3 | No anti-tumor activity* |
| MET-ADC#4 | No anti-tumor activity* |
| MET-ADC#5 | Tumor stasis* |
| MET-ADC#7 | Tumor growth inhibition^ |

*All of these experiments used 3 mg/kg x3 Q7D by i.p.
^All of these experiments used 1 mg/kg x3 Q7D by i.p.

Figure 7:
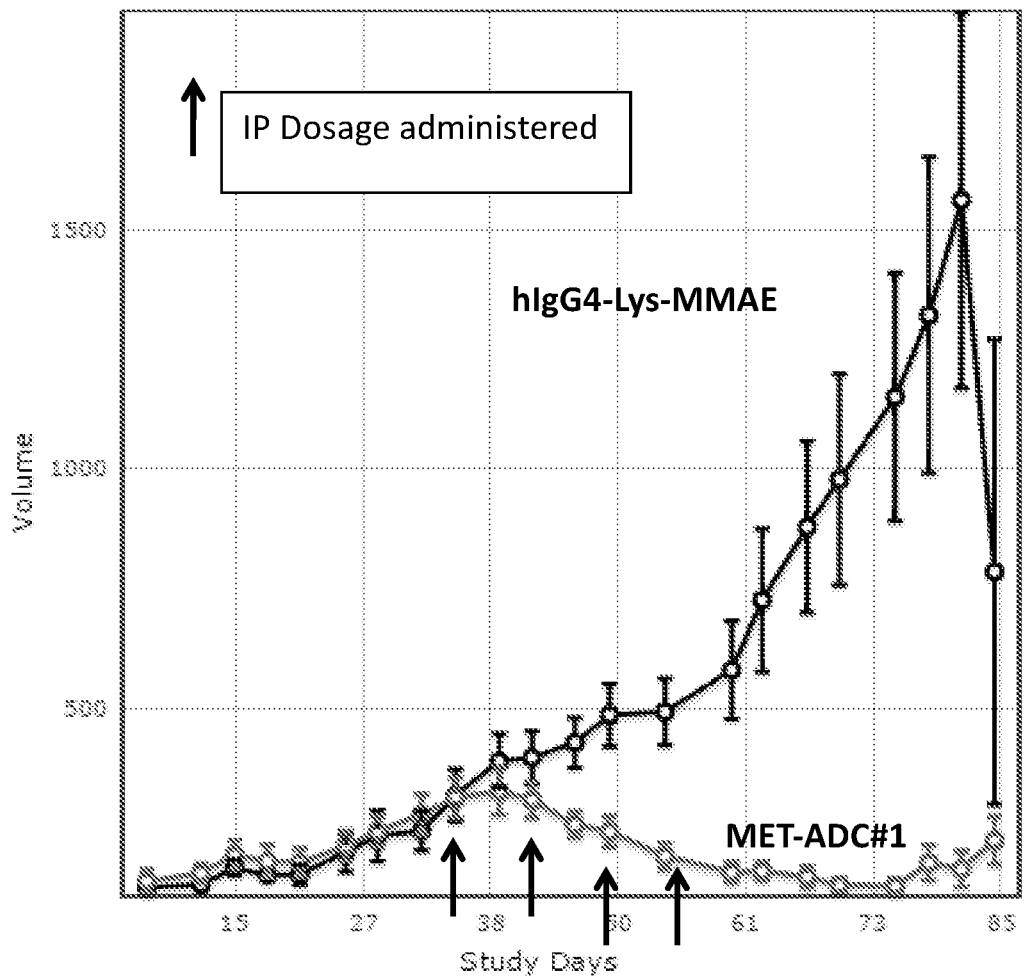
FIG. 7 shows the efficacy of MET-ADC #1 in an in vivo BxPC-3 xenograft model.
Figure 8:
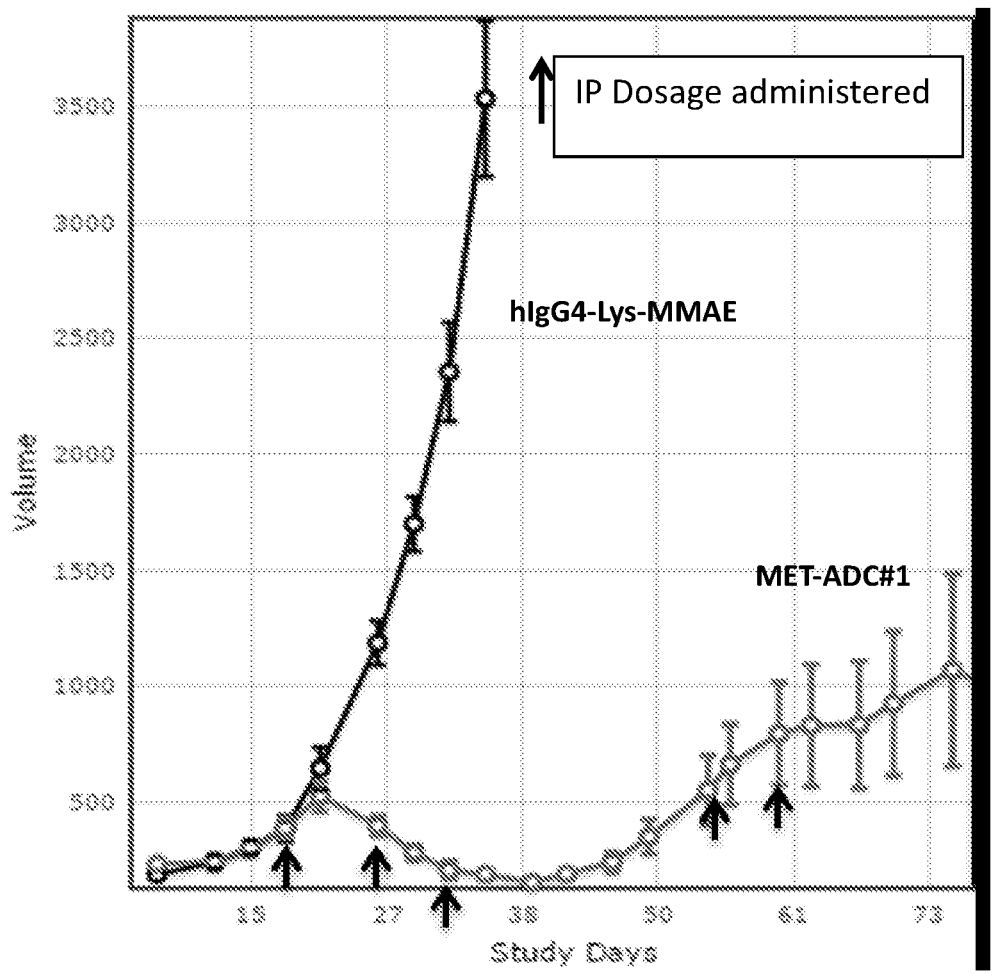
FIG. 8 shows the efficacy of MET-ADC #1 in an in vivo KP-4 xenograft model.

Part B:

Pancreatic cancer cells line BxPC-3 and KP-4 have a low level of cell surface MET expression. In a pancreatic cancer xenograft model generated essentially as described above in this Example 12 using either BxPC-3 or KP-4 cells, MET-ADC #1 showed dramatic anti-tumor activity as compared to the control hIgG4-Lys-ADC (see FIG. 7 or FIG. 8, respectively).

Part C:

The gastric cancer cell line Hs746T expresses cell surface MET at a moderate level and harbors MET exon 14 deletion. A gastric cancer xenograft model using Hs746T cancer cells may be developed in order to assess activity of MET-ADCs in this type of gastric cancer.

Figure 9:
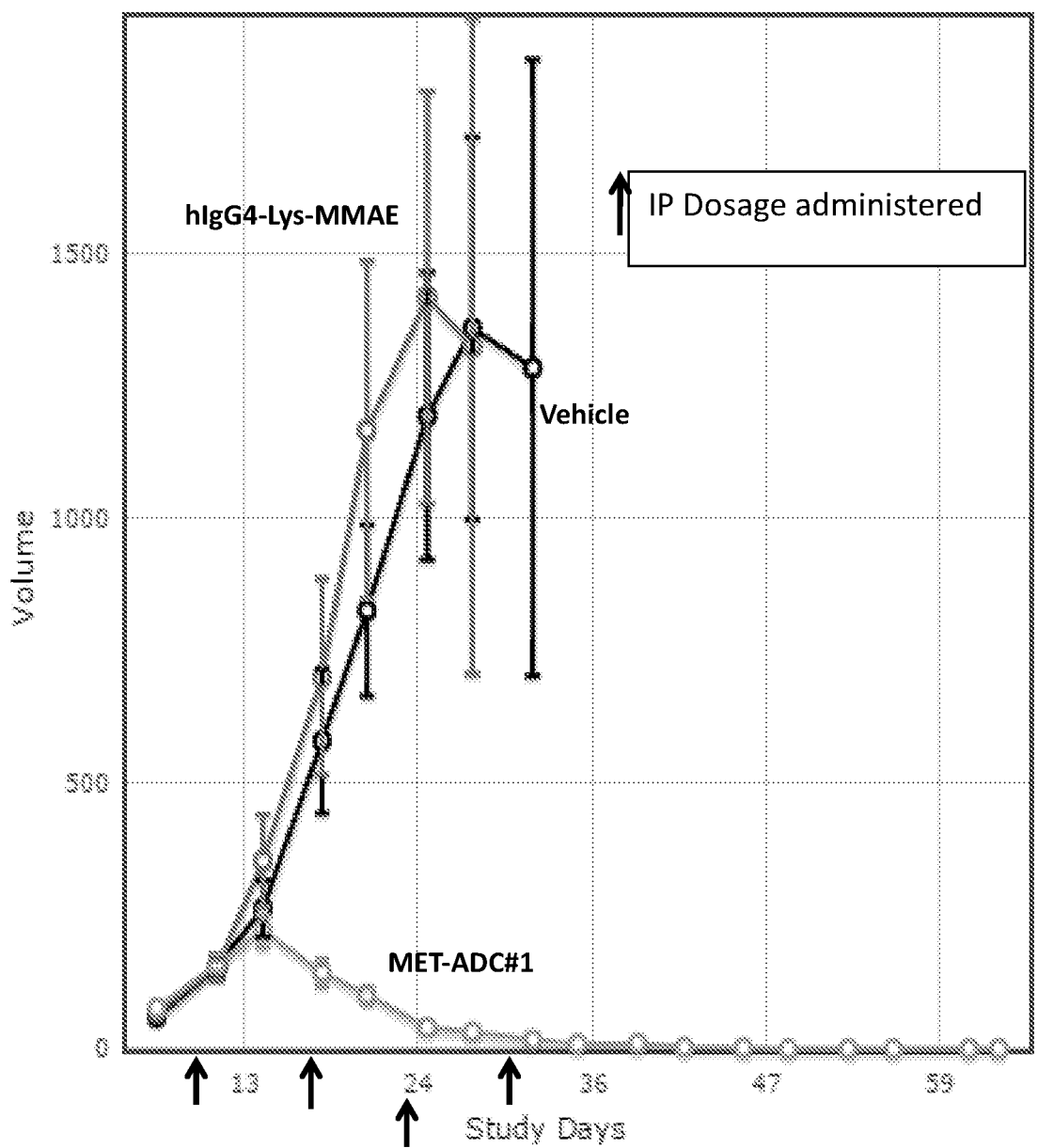
FIG. 9 shows the efficacy of MET-ADC #1 in an in vivo Hs746t xenograft model.
Figure 10:
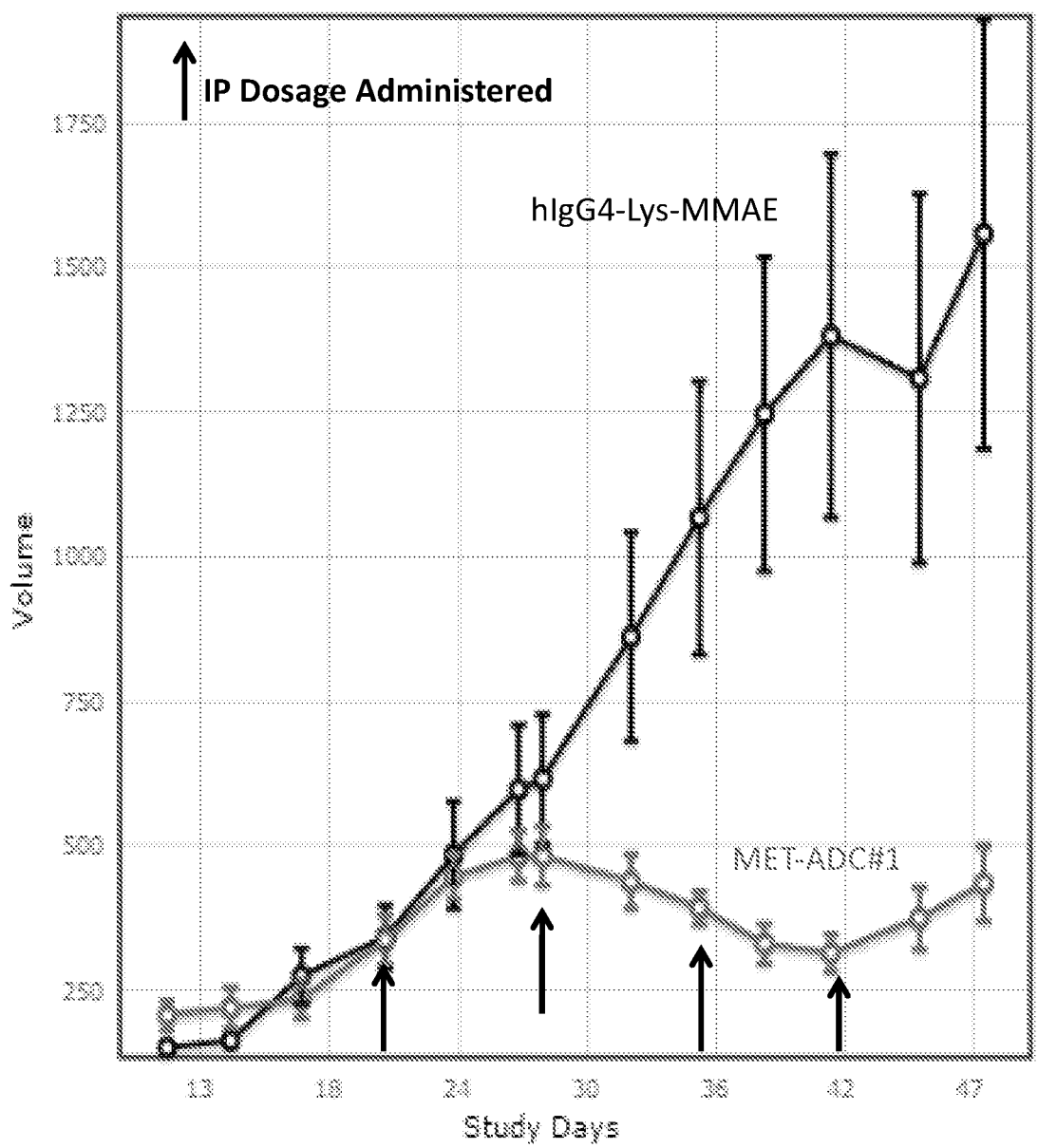
FIG. 10 shows the efficacy of MET-ADC #1 in an in vivo Calu-6 xenograft model.

A gastric cancer xenograft model using Hs746T cancer cells with MET exon 14 skipping was generated essentially as described above in this Example 12. Mice having Hs746T xenografts were treated with either IgG4 Lys-ADC control (3 mg/kg), and MET-ADC #1. Briefly stated, mouse Hs746T cell xenografts treated with 3 mg/kg of MET-ADC #1 once per week for 4 weeks resulted in significantly greater antitumor efficacy than the IgG4 Lys-MMAE control treatments (FIG. 9). The results showed that MET-ADC #1 induced durable and complete tumor regression in gastric cancer Hs746t model For Calu-6 non-small-cell-lung cancer model, initial tumor regression and stable disease status were observed following treatment with MET-ADC #1 (FIG. 10).

Example 13: Inhibition of Tumor Growth in Patient-Derived Xenograft (PDX) Models for Various Cancer Types Patient-derived tumor samples may be procured and tumor fragments derived from an individual patient can be implanted in a single immune-compromised mouse and allowed to grow until it reaches an approximate volume of 100-200 mm$^3$. MET-ADCs or hIgG4 isotype control ADC may administered once a week for 4 consecutive weeks at 5 mg/kg. Tumors may be measured via electronic caliper twice a week. Body weight can also be assessed regularly. Tumor volume may be calculated using the formula: $A^2 \times B \times 0.536$, where A is the smaller and B is the larger of perpendicular diameters.

Part A:

Pancreatic tumors are known in the art to overexpress MET and have more than 90% KRAS mutations (Yabar, C. S. and Winter, J. M., Gastroenterol Clin N Am 45: 429-445 (2016)). Pancreatic tumor samples from 40 human pancreatic cancer patients were individually implanted into different immunocompromised mice (i.e., each mouse carried one tumor derived from a patient's pancreatic tumor) essentially as described above in this Example 12. Thirty-eight of the 40 patient derived xenografts treated were assessed after weekly administration of 5 mg/kg of MET-ADC #1 for a total of 4 four doses. Almost all of the PDX tumors tested were shown to have moderate to high levels of MET expression on the tumor cell (data not shown).

Briefly stated, MET-ADC #1 profoundly reduced the volume of the pancreatic cancer PDX tumors when compared to control hIgG4-ADC-treated animals harboring PDX tumors:

CR: complete response (Tumor volume<=14 mm$^3$): 8

PR: partial response (% Regression<=–50% and tumor volume>14 mm$^3$): 9

SD: stable disease (% Delta T/C<=10% and % Regression>–50%): 7

PD: progressive disease (% Delta T/C>10%): 16

ORR: overall response rate (CR+PR over total 40): 43%

DCR: disease control rate: (CR+PR+SD over total 40): 60%

In experiments performed essentially as described above in this Example 13, MET-ADC #1 demonstrated better efficacy than the combination of gemcitabine and abraxane (i.e., the standard of care therapy for pancreatic cancer), with a nearly 2-fold reduction in Progression Free Survival (PFS) probability (Hazard ratio=0.56)(data not shown). The tumors were determined to have high levels of MET expressed on the cell surface. Generally pancreatic tumors exhibit KRAS mutation, high stroma content, and resistance to targeted therapies, chemotherapy, or small molecule MET inhibitors.

Part B:

Colorectal tumor samples from 37 human colorectal cancer patients were individually implanted into different immunocompromised mice (i.e., each mouse carried one tumor derived from a patient's pancreatic tumor) essentially as described above in this Example 13. Data from the 37 patient derived xenografts administered weekly with 1 or 3 mg/kg of MET-ADC #1 for a total of four doses were assessed. In stark contrast to the profound anti-tumor activity demonstrated by MET-ADC #1 in pancreatic cancer PDX models, MET-ADC #1 showed little activity in colorectal cancer PDX models when compared to control hIgG4-ADC-treated animals harboring PDX tumors. More specifically, MET-ADC #1 dosing resulted in 5.4% (2/37) Complete Response (CR) and 8% (3/37) Stable Disease (SD).

Figure 11:
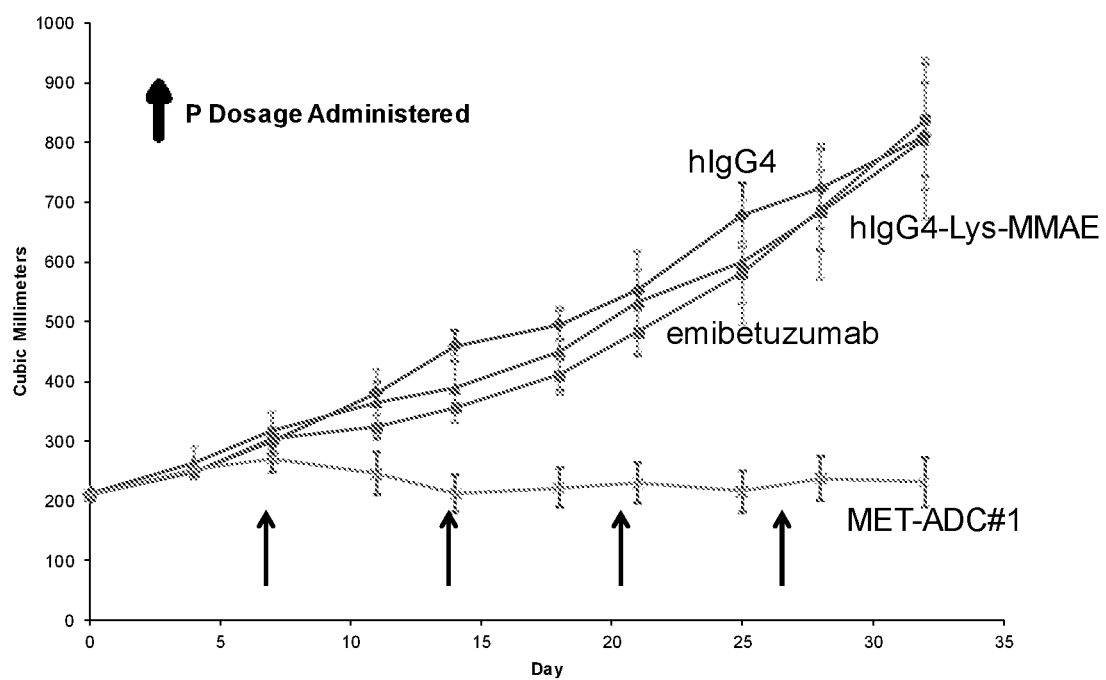
FIG. 11 shows the efficacy of MET-ADC #1 in an in vivo cholangiocarcinoma PDX model.

Part C:

Tumor samples from 4 human cholangiocarcinoma patients were individually implanted into different immunocompromised mice (i.e., each mouse carried one tumor derived from a patient's cholangiocarcinoma tumor) essentially as described above in this Example 13. The patient derived xenografts were administered weekly doses of 5 mg/kg of MET-ADC #1 for a total of four doses. As shown in FIG. 11, MET-ADC #1 dramatically inhibited tumor growth.

No significant loss of body weight during MET-ADC #1 treatment was observed for the studies described in this Example 13.

We claim:

1. An antibody-drug conjugate (ADC) of the formula:

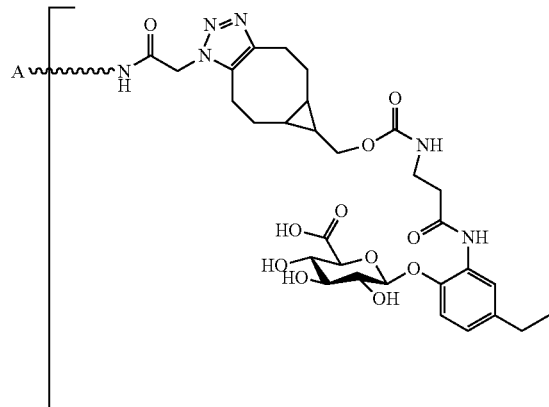

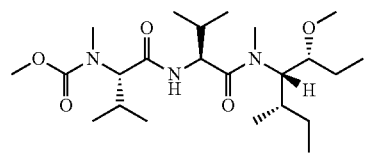

wherein A is an IgG4 antibody that binds MET and comprises:
 (a) a first heavy chain comprising the amino acid sequence of SEQ ID NO: 23, and
 (b) a first light chain comprising the amino acid sequence of SEQ ID NO: 9, and wherein n is 1 to 9,
or a salt thereof.

2. The ADC, or a salt thereof, according to claim 1 wherein A comprises:
 (a) the first heavy chain and a second heavy chain wherein each of the heavy chains comprises the amino acid sequence of SEQ ID NO: 23; and
 (b) the first light chain and a second light chain wherein each of the light chains comprises the amino acid sequence of SEQ ID NO:9.

3. The ADC, or a salt thereof, according to claim 1, wherein the first heavy chain forms an inter-chain disulfide bond with the first light chain, and the second heavy chain forms an inter-chain disulfide bond with the second light chain, and the first heavy chain forms two inter-chain disulfide bonds with the second heavy chain.

4. The ADC, or a salt thereof, of claim 1, wherein A is glycosylated.

5. A composition comprising a mixture of the ADCs, or salts thereof, according to claim 1, wherein n is 1 to 9 and the average DAR is 2 to 5.

6. The composition according to claim 5 wherein the average DAR is 2.9 to 4.

7. The composition according to claim 6 wherein the average DAR is 2.9 to 3.3.

8. The composition according to claim 5, wherein the composition induces internalization and/or degradation of cell surface MET expressed on a tumor cell.

9. The composition according to claim 5, wherein the composition lacks significant functional agonist activity in an in vitro proliferation, angiogenesis, and/or migration bioassay.

10. A pharmaceutical composition, comprising the ADC, or a salt thereof, according to claim 1, and a pharmaceutically acceptable carrier, diluent, or excipient.

11. A method of treating cancer, comprising administering to a patient in need thereof an effective amount of the ADC, or a salt thereof, according to claim 1.

12. The method according to claim 11 wherein the cancer is pancreatic, ovary, prostate, gastric, colorectal, esophageal, liver, bladder, renal, renal papillary, thyroid, cervical, head and neck, or lung cancer, NSCLC, SCLC, cholangiocarcinoma, melanoma or uveal melanoma in a human.

13. The method according to claim 11, wherein said cancer is characterized by comprising cells having one or more mutations selected from the group consisting of RAS, KRAS, BRAF, P53, MET exon 14, and/or PI3K mutations.

* * * * *